(12) United States Patent  
Inoue

(10) Patent No.: US 6,273,917 B1  
(45) Date of Patent: Aug. 14, 2001

(54) TRANSPLANTATION DEVICE

(76) Inventor: Kanji Inoue, 98-13, Miyazaki-cho Shimogamo, Sakyo-ku, Kyoto-shi, Kyoto 606-0802 (JP)

( * ) Notice: Subject to any disclaimer, the term of this patent is extended or adjusted under 35 U.S.C. 154(b) by 0 days.

(21) Appl. No.: 09/424,036

(22) PCT Filed: Mar. 27, 1998

(86) PCT No.: PCT/JP98/01374

§ 371 Date: Nov. 18, 1999

§ 102(e) Date: Nov. 18, 1999

(87) PCT Pub. No.: WO99/49927

PCT Pub. Date: Oct. 7, 1999

(51) Int. Cl.$^7$ .................................................... A61F 2/06
(52) U.S. Cl. .................... 623/23.64; 623/1.36; 623/1.15; 623/1.32
(58) Field of Search ...................... 623/1.15, 23.64–23.7, 623/1.36

(56) References Cited

U.S. PATENT DOCUMENTS

| | | |
|---|---|---|
| 3,304,557 | 2/1967 | Polansky . |
| 3,479,670 * | 11/1969 | Medell ................................ 623/1.15 |
| 4,313,231 | 2/1982 | Koyamada . |
| 4,747,849 * | 5/1988 | Galtier ................................ 623/1.15 |
| 4,872,874 | 10/1989 | Taheri . |
| 5,098,406 | 3/1992 | Sawyer . |
| 5,104,399 | 4/1992 | Lazarus . |
| 5,151,105 | 9/1992 | Kwan-Gett . |
| 5,183,085 | 2/1993 | Timmermans . |
| 5,207,695 | 5/1993 | Trout, III . |
| 5,234,456 | 8/1993 | Silvestrini . |
| 5,236,447 | 8/1993 | Kubo et al. . |
| 5,242,452 | 9/1993 | Inoue . |
| 5,290,305 | 3/1994 | Inoue . |
| 5,330,528 | 7/1994 | Lazim . |
| 5,383,926 | 1/1995 | Lock et al. . |
| 5,387,235 | 2/1995 | Chuter . |
| 5,507,767 | 4/1996 | Maeda et al. . |
| 5,507,771 | 4/1996 | Gianturco . |
| 5,554,181 | 9/1996 | Das . |
| 5,607,445 | 3/1997 | Summers . |
| 5,609,628 * | 3/1997 | Keranen ............................... 623/23.7 |
| 5,628,783 | 5/1997 | Quiachon et al. . |

(List continued on next page.)

FOREIGN PATENT DOCUMENTS

| | | |
|---|---|---|
| 4219949 | 12/1993 | (DE) . |
| 0472731 | 3/1992 | (EP) . |
| 2164562 | 3/1986 | (GB) . |
| 3-236836 | 10/1991 | (JP) . |
| 4-25755 | 2/1992 | (JP) . |
| 4-263852 | 9/1992 | (JP) . |
| 5-212121 | 8/1993 | (JP) . |
| 7-24072 | 1/1995 | (JP) . |
| 3009638 | 2/1995 | (JP) . |
| 6-63155 | 3/1995 | (JP) . |
| 91/12047 | 8/1991 | (WO) . |
| 95/05788 | 2/1995 | (WO) . |

Primary Examiner—David H. Willse  
Assistant Examiner—Suzette J. Jackson  
(74) Attorney, Agent, or Firm—Banner & Witcoff, Ltd.

(57) ABSTRACT

A front end wire ring $10_1$, and a rear end wire ring $10_2$ are arranged facing each other, and a tubular cover 7 connects the front and rear end wire rings $10_1$ and $10_2$, and an intermediate wire ring 12 is arranged between the front and rear end wire rings $10_1$ and $10_2$, wherein each of the wire rings $10_1$, $10_2$ and 12 is given flexibly foldable elasticity.

The front and rear end wire rings $10_1$ and $10_2$ and at least the intermediate wire rings 12 arranged adjacent to the front and rear end wire rings $10_1$ and $10_2$ is connected with the cover 7 through a film member 30 so that the wire rings $10_1$, $10_2$ and 12 can make a back and forth movement relative to the cover 7 within a certain range and that an annular gap formed between the wire rings $10_1$, $10_2$ and 12 and the cover 7 is liquid-tightly sealed.

19 Claims, 43 Drawing Sheets

U.S. PATENT DOCUMENTS

| | | |
|---|---|---|
| 5,665,117 | 9/1997 | Rhodes . |
| 5,676,671 | 10/1997 | Inoue . |
| 5,693,089 | 12/1997 | Inoue . |
| 5,755,772 | 5/1998 | Evans et al. . |
| 5,755,773 | 5/1998 | Evans et al. . |
| 5,782,904 | 7/1998 | White et al. . |
| 5,824,037 | 10/1998 | Fogarty et al. . |
| 5,843,162 | 12/1998 | Inoue . |
| 5,976,179 | 11/1999 | Inoue . |
| 6,007,575 * | 12/1999 | Samuels ................ 623/1.15 |
| 6,013,100 * | 1/2000 | Inoue ................... 623/23.7 |
| 6,162,244 * | 12/2000 | Braun et al. ............ 623/1.12 |

* cited by examiner

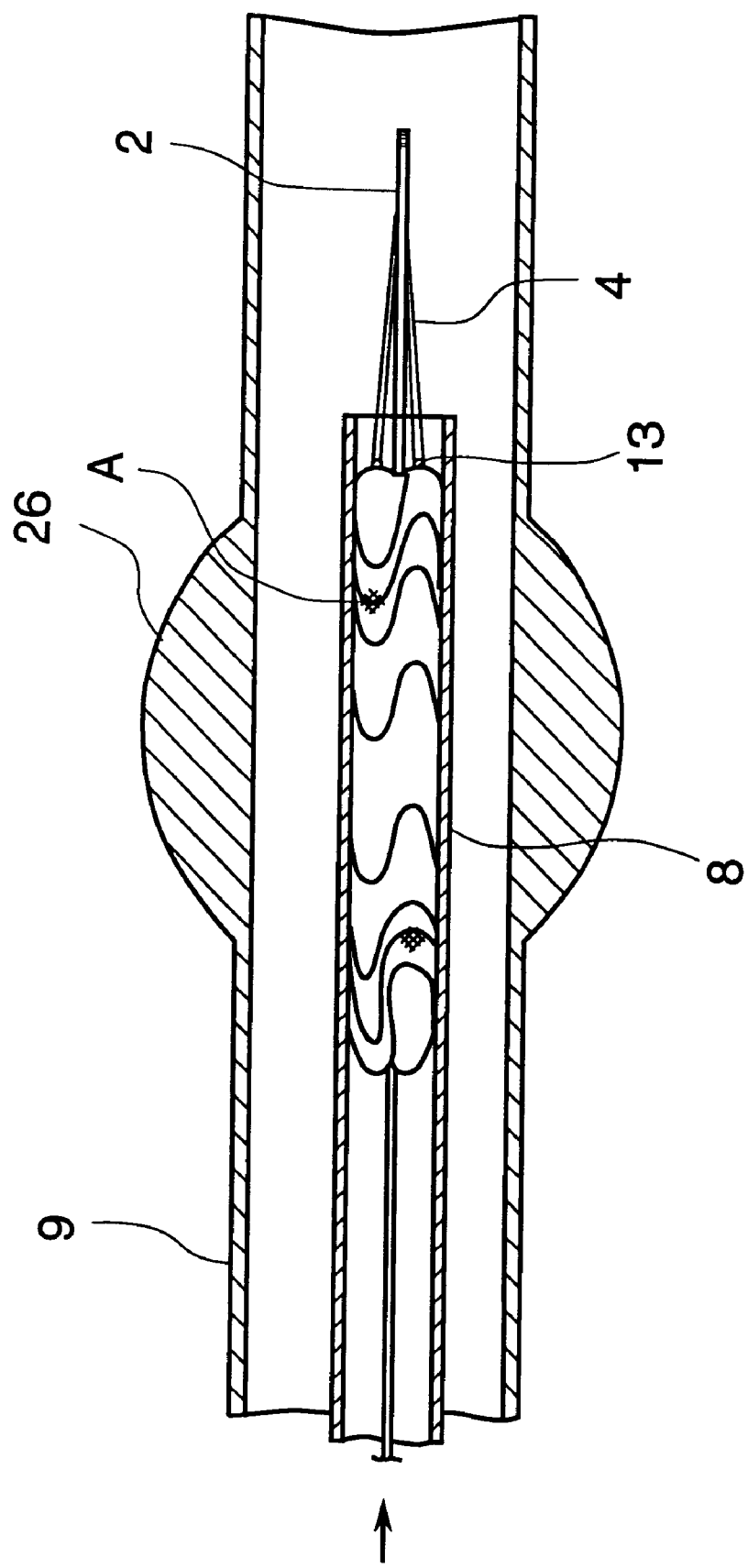

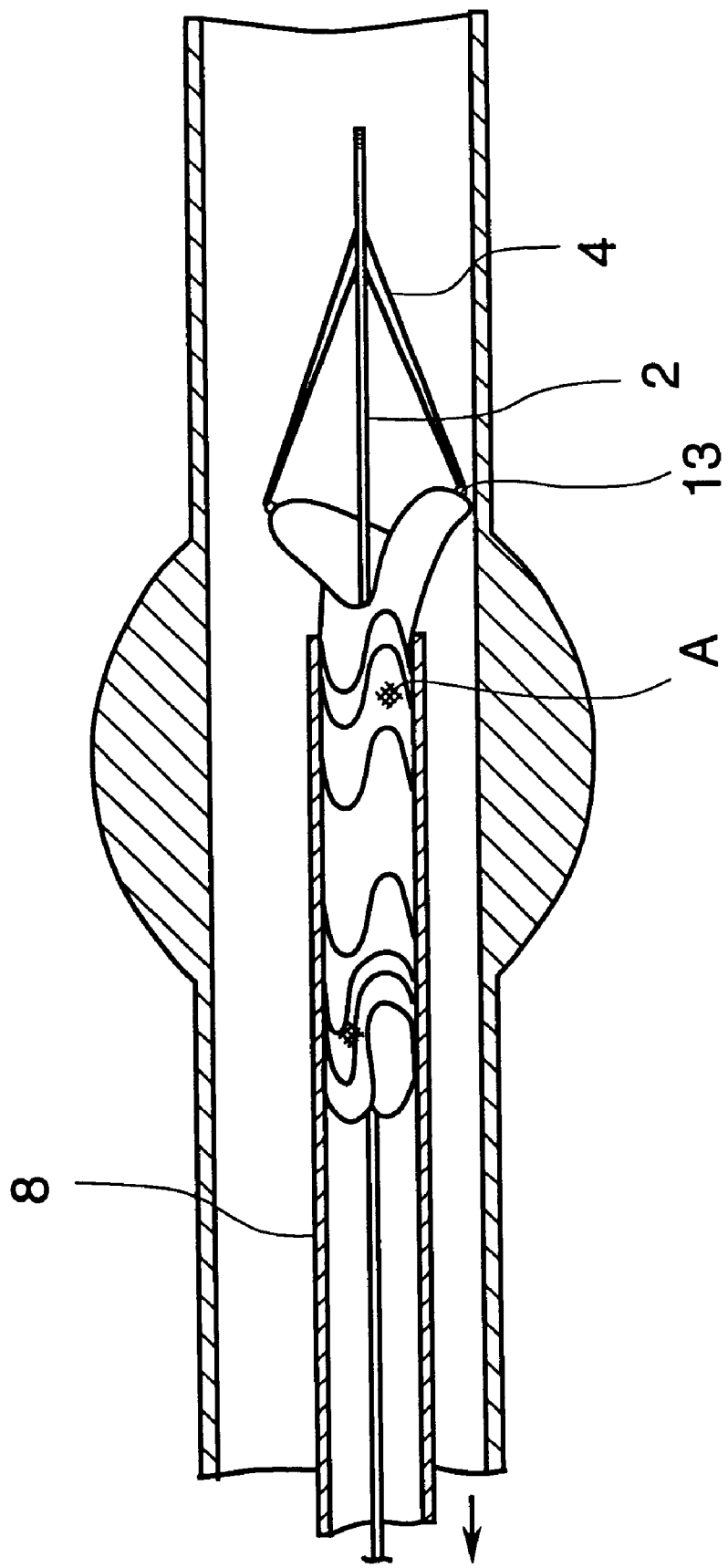

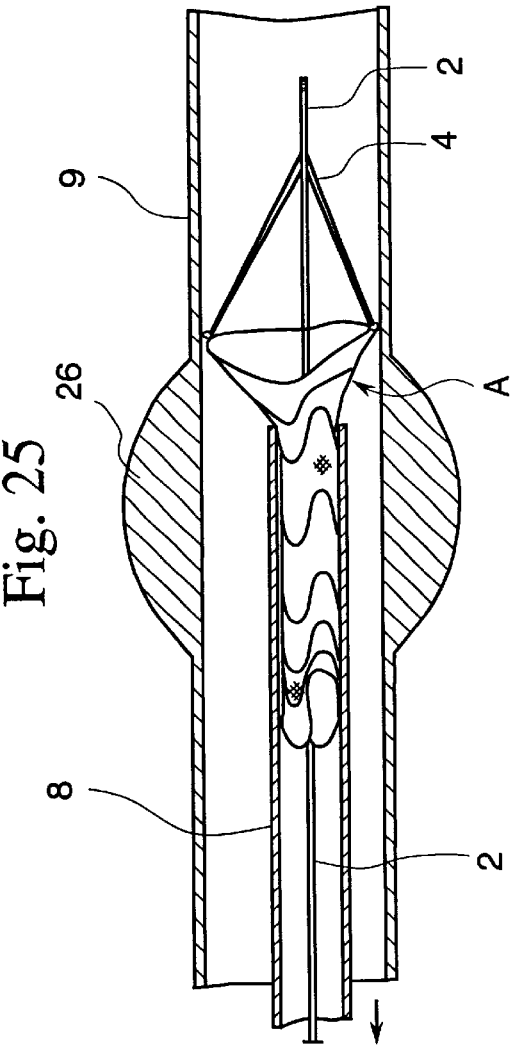
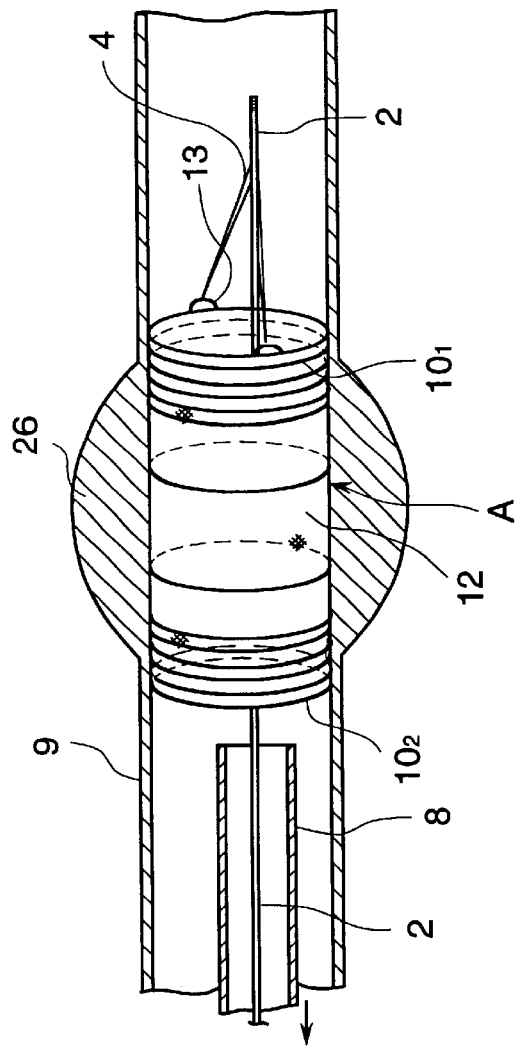

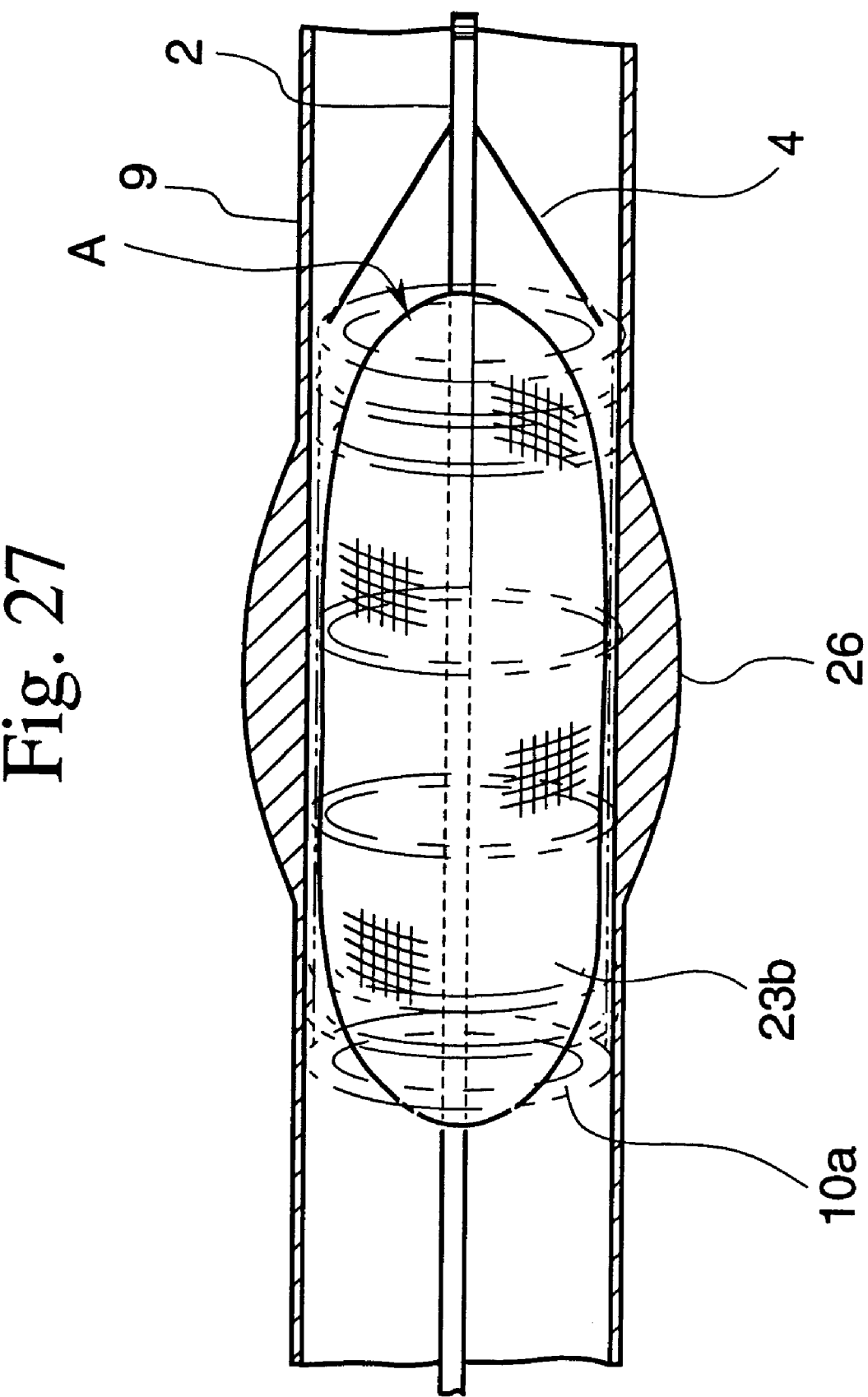

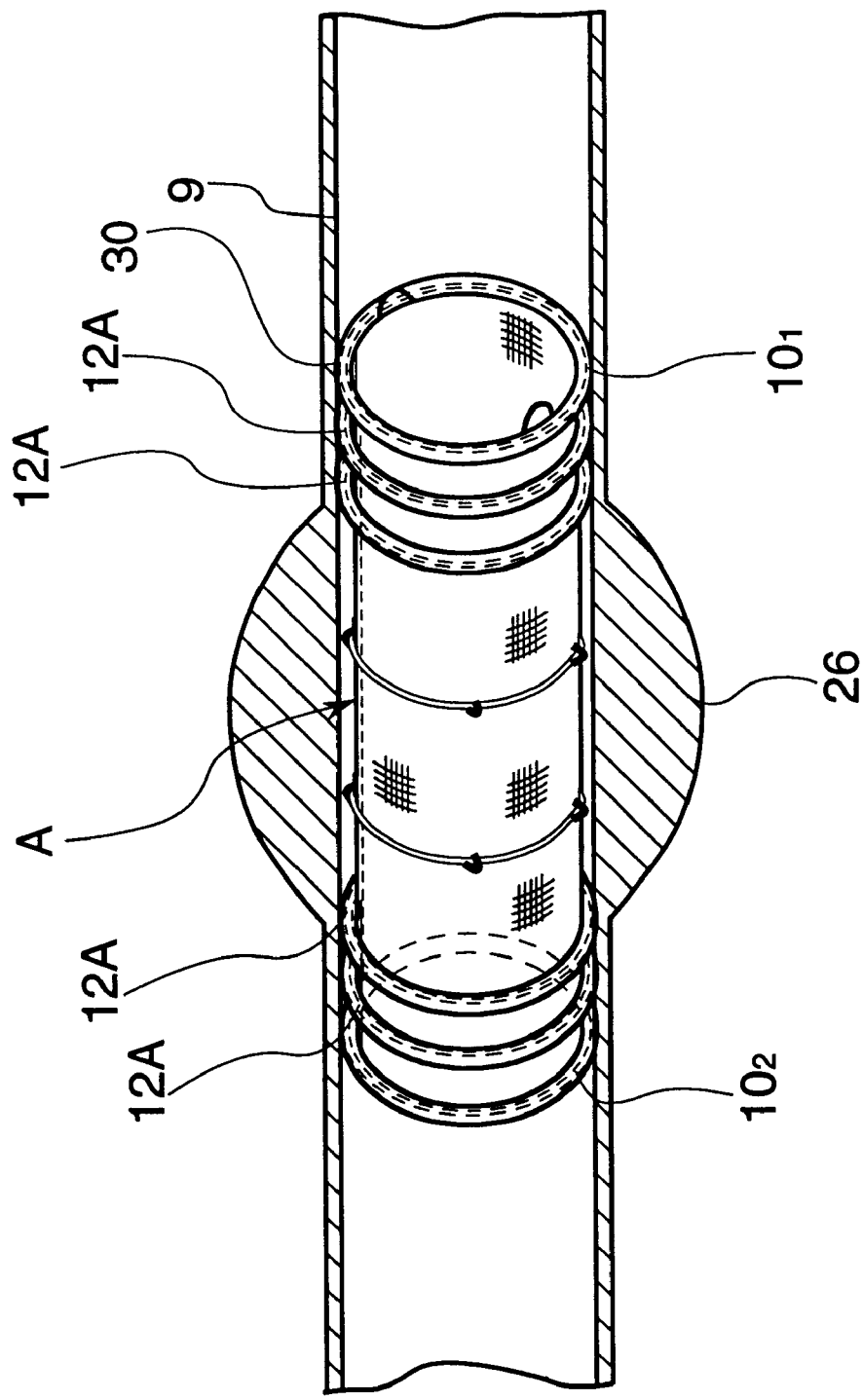

TRANSPLANTATION DEVICE

FIELD OF THE ART

This invention relates to appliances for medical treatment and, more particularly, to an appliance collapsible for insertion into a human organ and capable of resilient restoration (which will be referred to as "the appliance to be implanted" in this specification and claims).

BACKGROUND ART

The artificial blood vessel is an example of the appliance to be implanted. At present, treatment of, for example, aortic aneurysm is conducted by implanting an artificial blood vessel. In particular, the portion of a blood vessel which has an aneurysm is removed by resection, and an artificial blood vessel is implanted in place of the resected portion and connected to the remaining blood vessel by suturing or the like.

The above-mentioned method of surgically implanting the artificial blood vessel for treatment of aortic aneurysm, however, is highly dangerous. Especially, an emergency operation for treatment of a ruptured aneurysm has a low life-saving rate, and an operation of dissecting aortic aneurysm is difficult to conduct and has a high death rate.

Therefore, in order to treat these diseases without a surgical operation, a method has been developed of introducing a catheter into an appliance such as an artificial blood vessel in a collapsed condition into a human organ such as a blood vessel, and transporting the appliance to a desired position such as an affected or constricted portion thereof, where the appliance is released so as to be expanded and implanted there.

The appliance to be implanted is so constructed that a pair of flexibly foldable and elastic end wire rings are arranged, each of the end wire rings is connected by a tubular cover which is made of a sheet of flexible and tensile material and an intermediate wire ring is arranged between both of the end wire rings and fixedly connected to the above-mentioned tubular cover by suturing or with adhesive.

As a method of collapsing the appliance to be implanted, the following method is adopted in which a plurality of hooking means for a pull string to be passed are formed at every other dividing points each of which equally divides the circumference of the front end wire ring into an even number, the front end wire ring is folded into a wavy shape with the dividing points which are provided with a hooking means for a pull string forming forwardly directed peaks and the dividing points which are not provided with a hooking means for a pull string forming the bottoms of forwardly directed valleys, each of the intermediate wire rings and the rear end wire ring is folded into a wavy shape having the same phase as that of the front end wire ring and the whole artificial blood vessel is inserted into a catheter.

However, since the conventional appliance has an arrangement in which the cover is fixedly attached to the front and rear end wire rings along the circumference thereof, the cover tries to follow the movement of the front and rear end wire rings and forms wrinkles near the front and rear end wire rings when the appliance is folded into a wavy shape. Then the wrinkles gather around the folded portion of the wire rings, thereby to be bulky. This may hinder the appliance from being folded into a small size having an appropriate wavy shape. In addition, if the cover is folded into a small size and making wrinkles, the cover may fail to restore smoothly to the original shape in a target position when released. This may hinder the function of the appliance to be implanted as it is intended to.

In order to solve the above problems there is an appliance to be implanted having an arrangement in which a front and rear end wire rings are fixed to a cover not along all of the outer circumference thereof but at several intermittent points so that the front and rear end wire rings can move freely at a certain degree relative to the cover. The appliance to be implanted of this arrangement, however, might cause blood leakage from an annular gap between the cover and the wire rings, if used inappropriately.

The object of the invention is to solve all of the above-mentioned problems.

DISCLOSURE OF THE INVENTION

The appliance to be implanted in accordance with the invention comprises a front end wire ring, a rear end wire ring arranged facing to the front end wire ring, a tubular cover which connects the front and rear end wire rings, and an intermediate wire ring arranged between the front and rear end wire rings, in which each of the wire rings is given flexibly foldable elasticity, and is characterized by having an arrangement in which each of the front and rear end wire rings and at least the intermediate wire rings arranged adjacent to the front and rear end wire rings is connected with the cover through a film member so that each of the wire rings can make a back and forth movement relative to the cover within a certain range and that an annular gap formed between each of the wire rings and the cover is liquid-tightly sealed.

In this specification it is a matter of course that a wire ring means a wire made of material having a high resilient restoring force such as Ti—Ni alloy, a wire whose circumference is covered with a protective material such as a braid member is also included.

The arrangement of the film member may concretely be represented by being bag-shaped in which whole of each wire rings is wrapped and one end of the film member is attached to the cover almost to surround the outer circumference thereof so as to allow each of the wire rings to make a back and forth movement by making use of transformation of the film member. The film member may also be annular and each of the wire rings is attached along almost all of an outer circumferential end of the film member and an inner circumferential end of the film member is attached along almost all of the outer circumference of the cover so as to allow each of the wire rings to make a back and forth movement by making use of transformation of the film. The film member may also have a long and narrow space therein along the direction of back and forth in which each of the wire rings is wrapped so as to allow each of the wire rings to make a back and forth movement inside the space relative to the cover.

Another preferred arrangement of the film member may be represented by that having a wavy shape undulating along the direction of the circumference thereof and to a direction almost corresponding with a direction to which the wire rings are folded.

To improve a condition of the folded intermediate wire ring it is preferable that the intermediate wire ring is wrapped in a mesh member, which is attached along almost all of an outer circumference of the cover.

To improve an implanting condition of the appliance to be implanted, it is preferable that an expanding element is filled in a space between the film member and each of the wire rings.

As a preferable arrangement of the expanding element, it may be represented that the expanding element is a fiber which surrounds an outer circumference of a wire which mainly constitutes the wire rings or a powder which is filled in a space between the film member and the wire rings.

A concrete embodiment of the expanding element may be represented by super absorbing processed polymer which expands itself when it absorbs liquid.

To improve restoration force or attachability of the appliance to be implanted, it is preferable that an auxiliary wire ring is attached to the cover at a position almost corresponding to a position each of the wire ring is attached to the cover.

In this case, as a preferable implanting method of the appliance to be implanted, it is represented that the circumference of the auxiliary wire ring is divided into four or an even number over four, hooking means are formed for a front pull string to be passed through at every other dividing point, the auxiliary wire ring is folded into a wavy shape with the dividing points at which a hooking means is provided forming forwardly directed peaks and the other dividing points forming the bottoms of forwardly directed valleys, each of the other wire rings is folded into a wavy shape having the same phase as that of the auxiliary wire ring and the whole appliance to be implanted is inserted into a catheter.

In addition, as another preferable implanting method of the appliance to be implanted, it is represented that the circumference of a front end of the cover is divided into four or an even number over four and that hooking means are formed for a front pull string to be passed through at every other dividing point, the front end of the cover is folded into a wavy shape with the dividing points each of which is provided with a hooking means forming forwardly directed peaks and the other dividing points forming the bottoms of forwardly directed valleys, each of the front end wire ring, the intermediate wire rings and the rear end wire ring are folded into a wavy shape having the same phase as that of the front end of the cover and the whole appliance to be implanted is inserted into a catheter.

A preferable embodiment of the appliance to be implanted may be represented by an artificial blood vessel.

In accordance with the arrangement, it is possible to fold and restore in a body the appliance to be implanted smoothly, thereby to improve the implanted condition of the appliance to be implanted. In other word, when the wire rings are folded into a wavy shape, each of the wire rings can make a back and forth movement relative to the cover because of the film member through which each of the wire rings is connected with the cover. Then the cover does not have to follow the transformation of the wire rings completely, thereby to make a range in which the cover is folded small compared with the wire rings and to avoid forming a big winkle when folded. As a result of this, the cover is prevented from being bulky, resulting in a compact appliance to be implanted when folded. In addition, since the cover can be collapsed without bringing in a big wrinkle, it can be restored into a tubular shape smoothly and quickly when released in a target position in a blood vessel. This makes it possible to provide the appliance to be implanted with good transporting movement in a catheter and restoration in an appropriate condition in a target position, thereby to work effectively as it is intended to. The wire rings also are not hardly restricted from a free movement to transform, thereby to secure the wire rings an appropriate folding movement.

Since each of the wire rings is connected with the cover through the film member so that each of the wire rings can make a back and forth movement relative to the cover and an annular gap formed between each of the wire rings and the cover is liquid-tightly sealed by the film member, it can be prevented from blood leakage from the annular gap between the wire ring and the cover. In addition, since the wire rings can move freely to the cover, the wire rings gets a little influence from the cover and attaches tightly to an inner wall of an affected blood vessel without fail, thereby to improve a seal effect. This contributes to an improved condition of implanting the appliance to be implanted by preventing blood flowing into an affected portion such as an aneurysm, which steadily leads to an improved success rate of implantation.

The above-mentioned operation functions for not only a simple tubular shaped appliance to be implanted but also a bifurcated Y-shaped appliance to be implanted.

With a film member being bag-shaped in which whole of each wire rings is wrapped and one end of the film member being attached to the cover almost to surround the outer circumference thereof so as to allow each of the wire rings to make a back and forth movement by making use of transformation of the film member, a film member being annular and each of the wire rings being attached along almost all of an outer circumferential end of the film member and an inner circumferential end of the film member being attached along almost all of the outer circumference of the cover so as to allow each of the wire rings to make a back and forth movement by making use of transformation of the film member, or film member having a long and narrow space therein along the direction of back and forth in which each of the wire rings is wrapped so as to allow each of the wire rings to allow a back and forth movement inside the space relative to the cover, it is possible for the wire rings to make a back and forth movement relative to the cover with a simple arrangement. This arrangement also makes it possible to effectively prevent from blood leakage through an annular gap between the cover and the wire rings since both ends of the appliance to be implanted make close adherence to an internal wall of a human organ.

In addition, if the film member has a wavy shape undulating along the direction of the circumference and to a direction corresponding with a direction to which the wire rings are folded, a margin for folding each of the wire rings can be made bigger, which makes a range of movement of the cover smaller when folded. As a result, it can effectively prevent the cover from bringing about wrinkles, thereby to secure an improved folding movement and restoration for the appliance to be implanted.

If the intermediate wire ring is wrapped in a mesh member, which is attached along almost all of an outer circumference of the cover, the intermediate wire ring is free from dragging resistance from the cover. This secures the intermediate wire ring to make a free movement so as to be collapsed with ease. This also prevents the intermediate wire ring from being folded inappropriately.

If an expanding element is filled in a space between a film member and each of the wire rings, both ends of the appliance to be implanted can tightly be attached to an inner wall of a human organ when inserted and released into the human organ when the expanding element is made to expand. This arrangement is effective to prevent blood leakage from the both ends of the appliance to be implanted.

If the expanding element is a fiber which surrounds an outer circumference of a wire which mainly constitutes the wire rings or a powder which is filled in a space between the film member and the wire rings, it is easy to store and expand the expanding element in the space between the film member and the wire ring.

If the expanding element is super absorbing processed polymer which expands itself when it absorbs liquid, blood flows into the film member when the appliance to be implanted is released in a body, thereby to attach both ends of the appliance to be implanted to an inner wall of the affected human organ with ease. If the appliance to be implanted is, for example, used as an artificial blood vessel, leakage of blood from both ends of the artificial blood vessel can effectively be prevented.

If an auxiliary wire ring is attached to the cover at a position corresponding to a position each of the wire ring is attached to the cover, the restoration force and the attachability to a human body of the appliance to be implanted can effectively be improved with cooperation with the wire rings when released in a body.

In order to implant the appliance to be implanted into a human body if a method is used which comprises that the circumference of the auxiliary wire ring or a front end of the cover is divided into four or an even number over four, hooking means are formed for a front pull string to be passed through at every other dividing point, the auxiliary wire ring or the front end of the cover is folded into a wavy shape with the dividing points each of which is provided with a hooking means forming forwardly directed peaks and the other dividing points forming the bottoms of forwardly directed valleys, each of the other wire rings is folded into a wavy shape having the same phase as that of the auxiliary wire ring or the front end of the cover and the whole appliance to be implanted is inserted into a catheter, it is possible to fold the appliance to be implanted into a small size and to transport the appliance to be implanted through a catheter, thereby to improve practicality and a property of general purpose of the appliance to be implanted drastically.

If the appliance to be implanted is an artificial blood vessel, an operation and an effect of the invention can sufficiently be produced.

BRIEF DESCRIPTION OF THE DRAWINGS

FIG. 23 is a cross-sectional view showing the artificial blood vessel transported to an affected portion.

FIG. 24 shows a step to release the artificial blood vessel at the affected portion in the blood vessel.

FIG. 25 shows a step to release the artificial blood vessel at the affected portion in the blood vessel.

FIG. 26 is a cross-sectional view showing the artificial blood vessel released at the affected portion in the blood vessel.

FIG. 27 shows a step to expand the artificial blood vessel by means of a balloon catheter.

FIG. 28 is a cross sectional view showing the artificial blood vessel released at the affected portion in the blood vessel.

BEST MODES OF EMBODYING THE INVENTION

The invention will be described in detail with reference to the embodiments thereof shown in the accompanying drawings.

Figure 1:
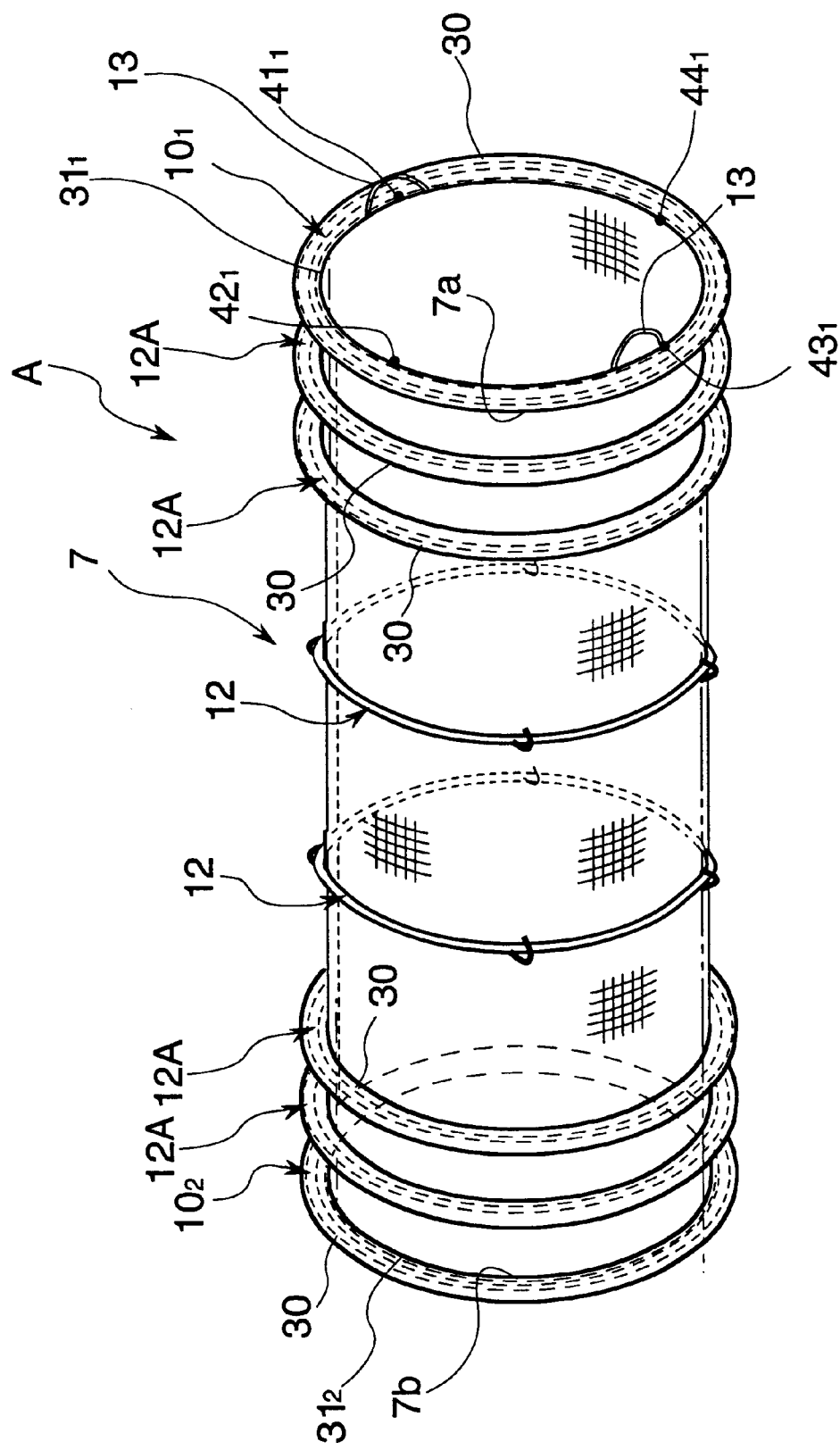
FIG. 1 is a perspective view of an artificial blood vessel in accordance with one embodiment of the invention.

The artificial blood vessel A as the appliance to be implanted, which is collapsed by the method in accordance with this invention, comprises, as shown in FIG. 1, a cover 7, front and rear end wire rings $10_1$, $10_2$ arranged at the front and rear ends 7a, 7b of the cover 7, intermediate end wire rings 12A arranged near the front and rear end wire rings $10_1$, $10_2$, intermediate wire rings 12 arranged between the intermediate end wire rings 12A and a film member 30 which attaches the front and rear end wire rings $10_1$, $10_2$, the intermediate end wire rings 12A and the intermediate wire rings 12 to the cover 7 so that the wire rings $10_1$, $10_2$, 12A, 12 can make a back and forth movement relative to the cover 7.

In this embodiment a wire made of material having a high resilient restoring force such as Ti—Ni alloy will be referred to as wire rings.

Figure 2:
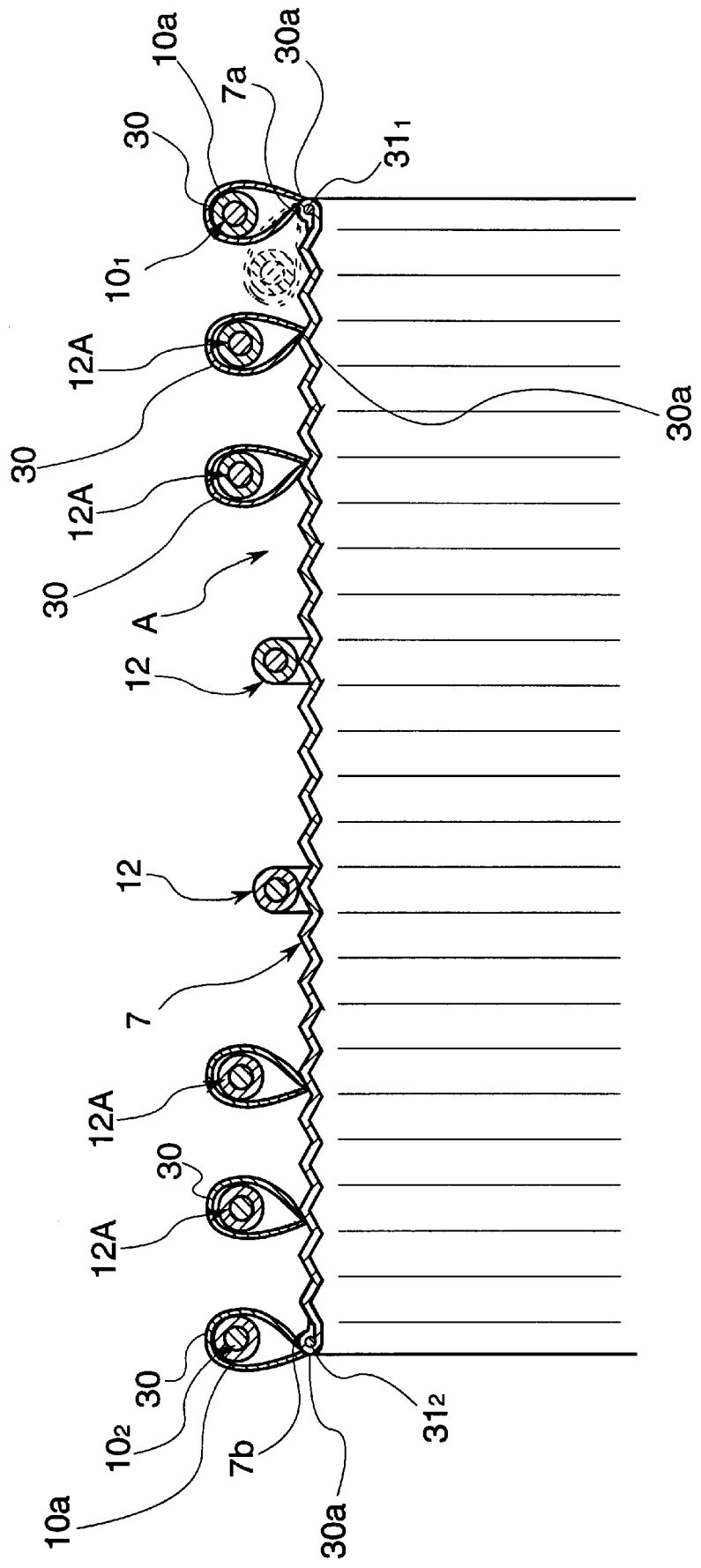
FIG. 2 is a vertical cross-sectional view of part of the artificial blood vessel.

The cover 7, as shown in FIG. 2, consists of a flexible, tensile sheet shaped into a tube of bellows, the normal diameter of which generally corresponds to the shape of that portion of the human blood vessel at which the artificial blood vessel A is to be implanted. The sheet of the cover 7 is, for example, of warps extending in the axial direction of the artificial blood vessel A woven with wefts extending in the circumferential direction thereof, wherein the warps are of mono-filament made of polyester (about 15 denier) and the wefts are of multi-filament made of a plurality of superfine filaments (about 50 denier) interwoven. The wefts are additionally woven with thread of polyethylene of about 10 denier to make the sheet of the cover 7 thinner and stronger. The cover 7 is coated, if necessary, with waterproof material, for example, collagen or albumin, to prevent leakage of blood. In addition, auxiliary front and rear end wire rings $31_1$, $31_2$ are fixed to the cover 7 by suturing or with adhesive at positions of the front and rear ends 7a, 7b which correspond to positions at which the front and rear end wire rings $10_1$, $10_2$ are fixed to the cover 7. The auxiliary front and rear end wire rings $31_1$, $31_2$ are made of a wire which is thinner than that constitutes the front and rear end wire rings $10_1$, $10_2$. The auxiliary front and rear end wire rings $31_1$ $31_2$ give the artificial blood vessel A restoring force and attachability to a body. As shown in FIG. 1, loop-shaped front hooking means 13 are formed at a pair of dividing points $41_1$ and $43_1$ facing each other across the axis of four dividing points $41_1$, $42_1$, $43_1$, $44_1$ each of which equally quadrisects the circumference of the auxiliary front end wire ring $31_1$. The hooking means 13 in accordance with the embodiment are formed of string. It may not necessarily be of string, but a hole directly formed on the cover 7 may be utilized as the hooking means, if there is no trouble.

The front and rear end wire rings $10_1$, $10_2$ are axially spaced apart and arranged face to face and inner diameter of them is set to be larger than that of the abovementioned cover 7. The front and rear end wire rings $10_1$, $10_2$ are put in a bag-shaped film member 30 which is mounted on the front end 7a or the rear end 7b of the cover 7 so as to make a back and forth movement relative to the cover 7 as shown FIG. 2. The film member 30 is bag-shaped in which whole of each of the front and rear end wire rings $10_1$, $10_2$ is wrapped up and one end 30a of the film member 30 is attached to the cover 7 almost to surround the outer circumference thereof with thread or by adhesive so as to allow each of the front and rear end wire rings $10_1$, $10_2$ to make a back and forth movement by making use of transformation of the film member 30 and to liquid-tightly seal a ring-shaped gap between the front and rear end wire rings $10_1$, $10_2$ and the cover 7. More specifically, the film member 30 makes a back and forth movement relative to the cover 7 through the end 30a thereof, as shown in imaginary lines in FIG. 2, when the artificial blood vessel A is inserted into or released from a catheter in a collapsed condition. At that time the front and rear end wire rings $10_1$, $10_2$ wrapped in the film member 30 also make a back and forth movement relative to the cover 7. The film member 30 used in this embodiment is made of the same material as the sheet which constitutes the cover 7. The circumferences of the front and rear end wire rings $10_1$, $10_2$ are covered with protective braid members 10a, as shown in FIG. 2. The protective braid members 10a are made of, for example, polyester fiber tied up in a bundle like cotton. If a flexible protective member such as the braid member 10a is circumferentially arranged on the front and rear end wire rings $10_1$, $10_2$, the inner wall of a human organ can effectively be prevented from getting damaged by direct contact with the front and rear end wire rings $10_1$, $10_2$.

A plurality of intermediate wire rings 12 have an arrangement of being wrapped with protective film such as cloth or braid members 10a like the above-mentioned front and rear end wire rings $10_1$, $10_2$, and are arranged general-equidistantly spaced between the front and rear end wire rings $10_1$ and $10_2$. Each of the intermediate wire ring 12 is fixed to the cover 7 at four specified positions on the circumference thereof with thread, adhesive or the like and help keep the tubular shape of the cover 7 together with the above-mentioned front and rear end wire rings $10_1$, $10_2$. In this embodiment each two of the intermediate end wire rings 12A arranged near the front and rear end wire rings $10_1$ and $10_2$ are set to have a larger inner diameter than the inner diameter of the cover 7 and wrapped in a bag-shaped film member 30 so as to allow a back and forth movement relative to the cover 7 like the front and rear end wire rings $10_1$, $10_2$. The film member 30 is attached to the cover 7 at one end 30a thereof almost to surround the outer circumference thereof with thread or by adhesive so as to allow each of the intermediate end wire rings 12A to make a back and forth movement through the film member 30 and to liquid-tightly seal a ring-shaped gap between the intermediate end wire ring 12A and the cover 7.

In order to implant the artificial blood vessel A of the above-mentioned arrangement into a target organ of a human body, a device B for transporting the artificial blood vessel (see FIG. 3) is used to transport the artificial blood vessel A to the target organ of the human body through the catheter 8 and a device C for introducing the artificial blood vessel (see FIG. 4) is used to introduce the artificial blood vessel A into the catheter 8.

Figure 3:
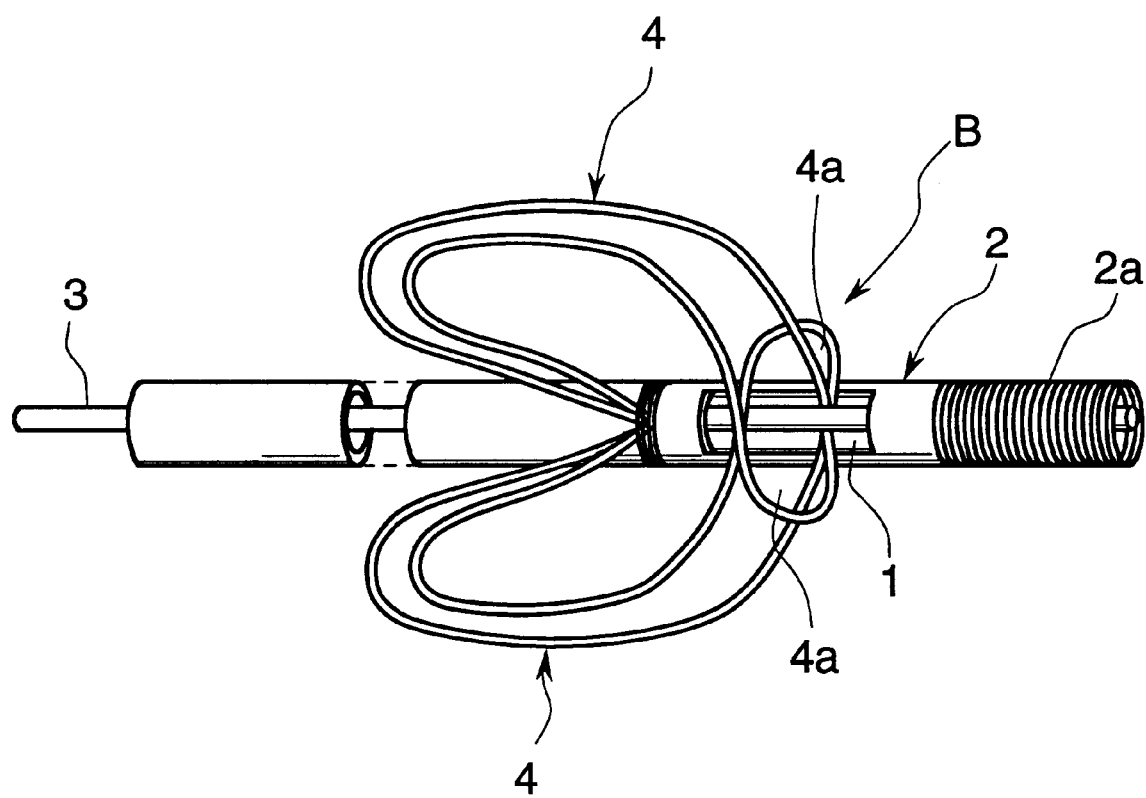
FIG. 3 is a perspective view of a device for transporting the artificial blood vessel, used in the embodiment.

The device B for transporting the artificial blood vessel, as shown in FIG. 3, comprises a flexible metallic tube 2 whose front end portion is connected to a helical spring 2a for guiding, a side window 1 formed adjacent the front end of the tube 2, a pair of strings 4 having both their ends fixed to the tube 2 adjacent the side window 1 and their middle portions formed into loops to be looped portions 4a, and a length of wire 3 slidably inserted into the tube 2. Instead of the above-mentioned helical spring 2a for guiding, a flexible tube may be used. The device for transporting the artificial blood vessel may comprise the tube 2 and a length of wire 3 alone, which will be described later.

Figure 4:
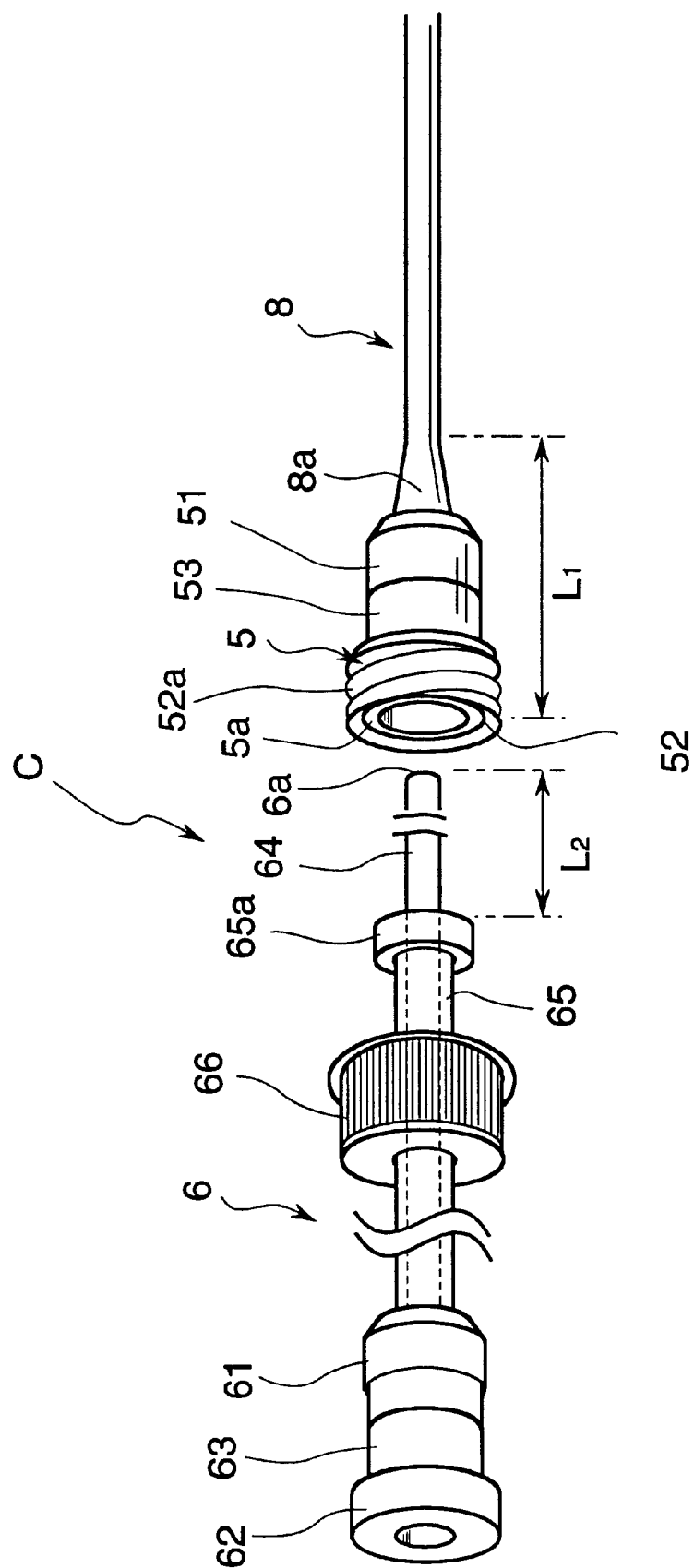
FIG. 4 is a perspective view of a device for introducing the artificial blood vessel, used in the embodiment.
Figure 5:
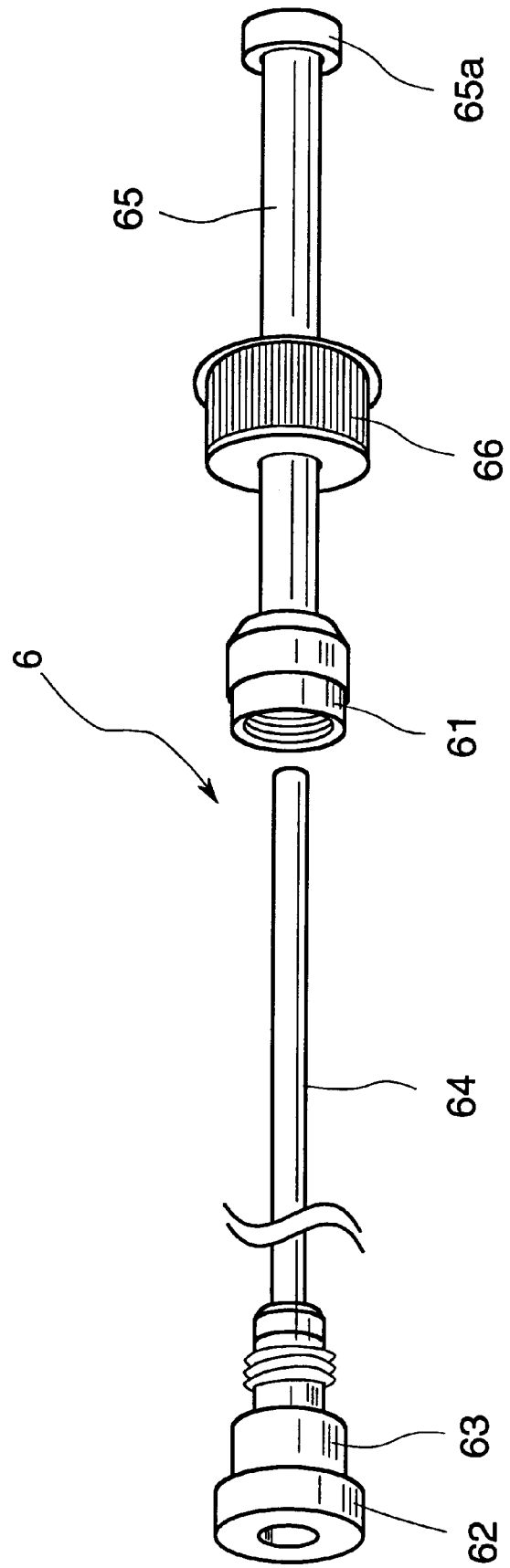
FIG. 5 is a perspective view of a cartridge which constitutes the device for introducing the artificial blood vessel.
Figure 6:
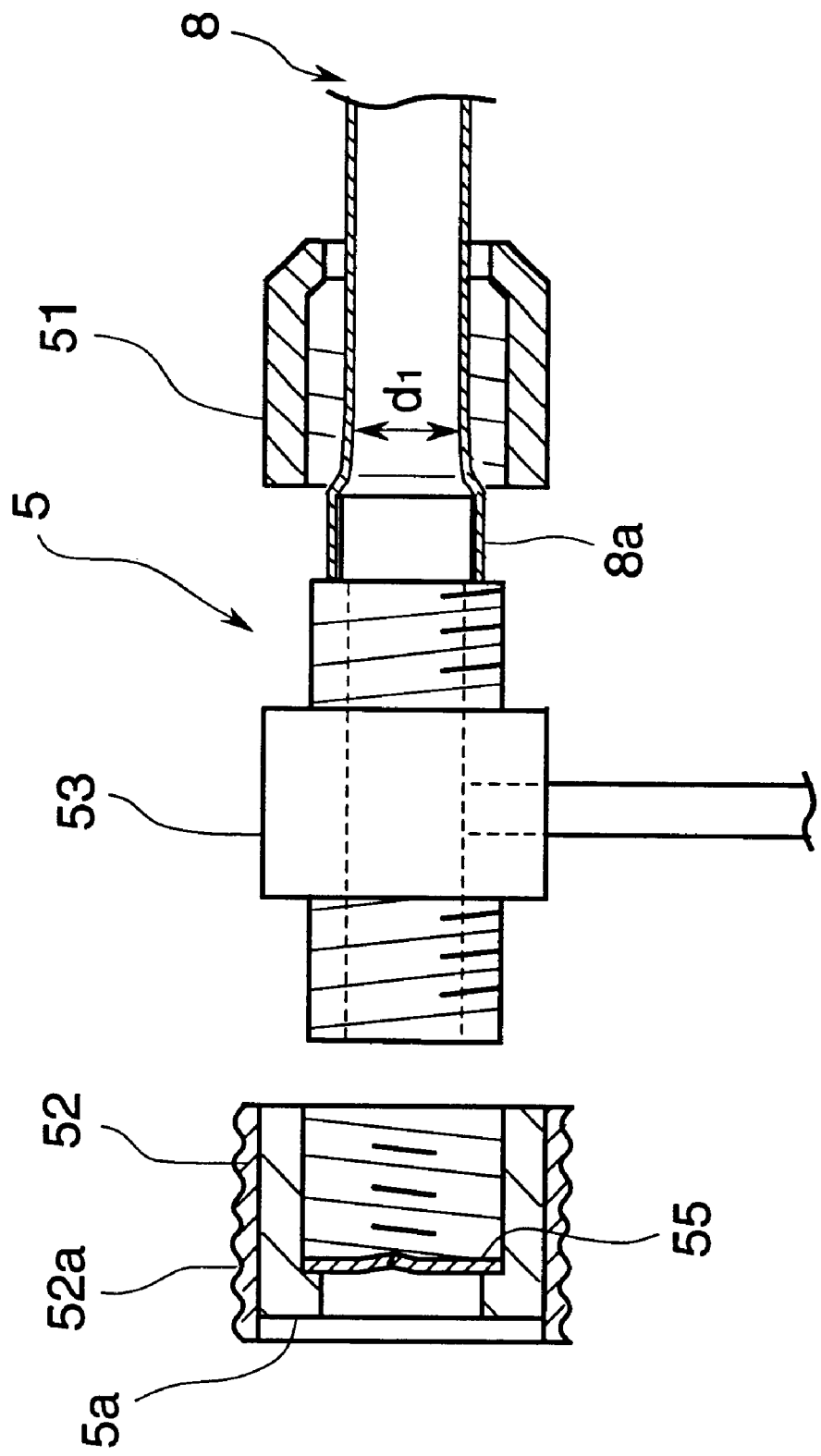
FIG. 6 is an enlarged vertical cross-sectional view of part of the attachment shown in FIG. 4.
Figure 7:
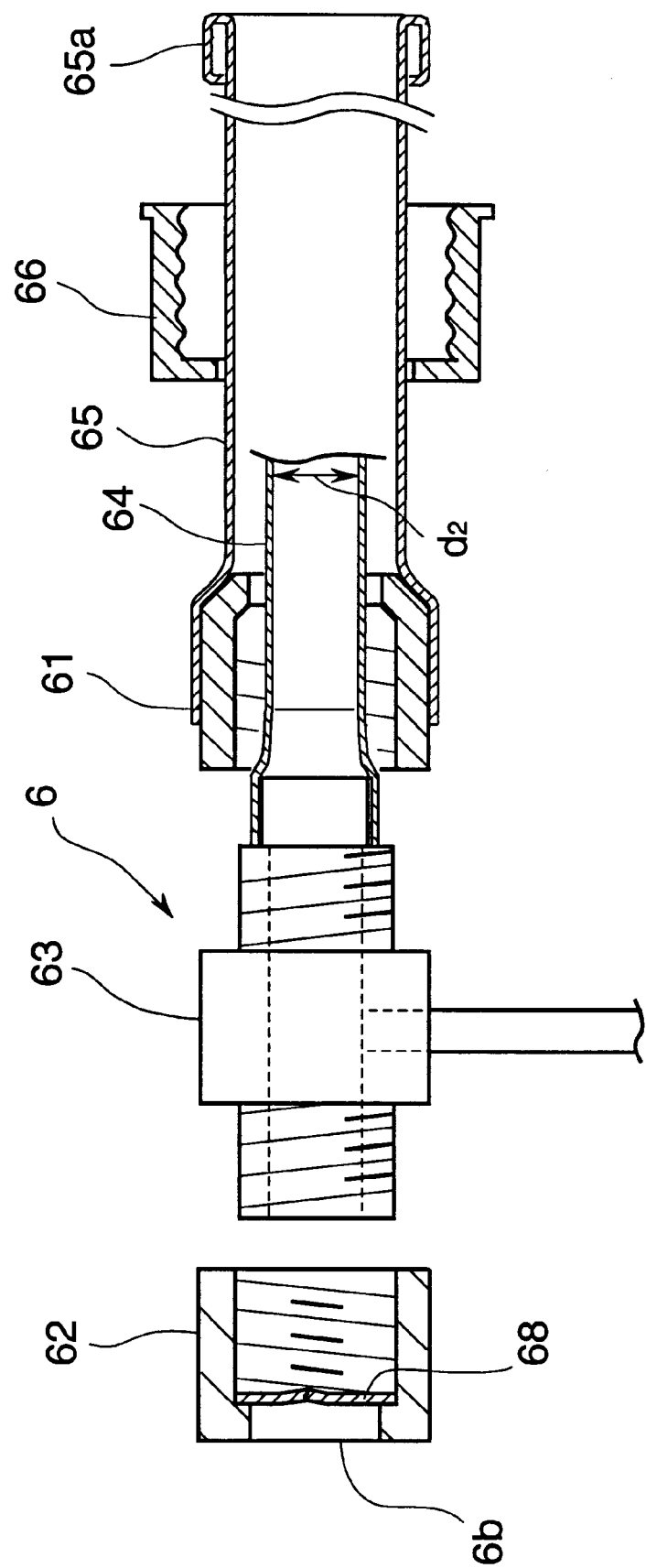
FIG. 7 is an enlarged vertical cross-sectional view of part of the cartridge shown in FIG. 4.

The device C for introducing the artificial blood vessel, as shown in FIG. 4, comprises an attachment 5 integrally connected to the catheter 8 through an open end 8a thereof, and a cartridge 6 removably attached to the attachment 5. As shown in FIGS. 4 and 6, the attachment 5 comprises a first and a second annular member 51, 52 which are internally threaded to form female screws, and a third annular member 53 which is externally threaded to form male screws at opposite ends, which engages the above-mentioned female screws thereby to connect the internal space of the first and the second annular members 51, 52 at its male screw part. The catheter 8 is formed to have an open end 8a of a little larger diameter and attached to the tip of the male screw of the above-mentioned third annular member 53 at its open end 8a. Then the third annular member 53 is liquidtightly joins the interior of the open end 8a of the catheter 8. Inside the second annular member 52 provided is a check valve 55 made of elastic membrane to close the open end thereof and outside of it fittingly provided is a cylinder-shaped helical member 52a having a helical groove. The cartridge 6, as shown in FIGS. 4, 5 and 7, comprises first and second annular members 61, 62 which are internally threaded to provide internal female screws, a third annular member 63 which is externally threaded to form male screws at opposite ends, which engage the abovementioned female screws at opposite ends to connect the first and second annular members 61, 62, a straw member 64 whose rear end is liquidtightly attached to the tip of one of the male screw parts of the third annular member 63 and the front end of which is extending toward the direction to which the cartridge 6 is inserted, a cylinder-shaped guide pipe 65 having an internal diameter which can contain the straw member 64, one of whose ends integrally connected to the first annular member 61 and the other end thereof provided with a large portion 65a, and a cap 66 which is slidably movable along the axial direction of the guide pipe 65 and loosely fit to the external of the guide pipe 65 and inside of which formed is a helical groove which helically connects the helical member 52a of the attachment 5. A check valve 68 made of elastic membrane is provided inside the second annular member 62 to close the open end thereof.

Figure 21:
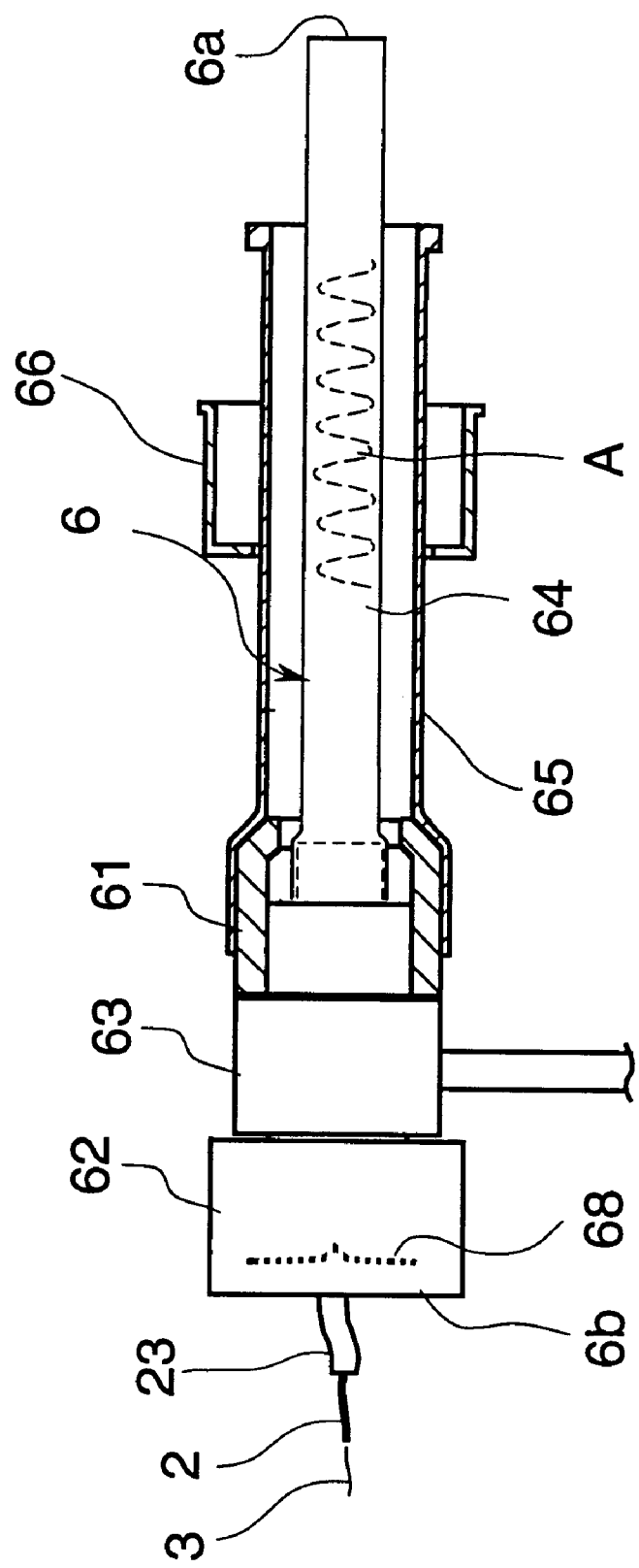
FIG. 21 is a partly cut-out side view showing the cartridge from which the funneled tube is drawn out.

As shown in FIG. 4, the straw member 64 of the cartridge 6 is so constructed that the front end portion 6a thereof is removably fitted into the rear end portion 5a of the attachment 5. In particular, as shown in FIGS. 4, 6 and 7, the bore diameter $d_1$ adjacent the open end 8a of the catheter 8 is set generally the same as or a little larger than the bore diameter $d_2$ of the straw member 64 of the cartridge 6, and the length $L_2$ of the straw member 64 extending from the large portion 65a of the guide pipe 65 is set approximately equal to the length Li between the end portion 5a of the attachment 5 and the position a little deep from the open end 8a of the catheter 8. The large portion 65a formed on one end of the cartridge 6 is made abutting engagement with the end portion 5a of the attachment 5 with the cap 66 helically mounted to the outer surface of the cylinder-shaped helical member 52a as shown in FIG. 21, and the front end portion 6a of the straw member 64 is inserted into the open end 8a of the catheter 8 so that the straw member 64 is smoothly connected to inside of the open end 8a of the catheter 8. The abovementioned check valves 55, 68 are made of elastic membrane, in each of which a normally closed hole, not shown in drawings, is formed.

Figure 8:
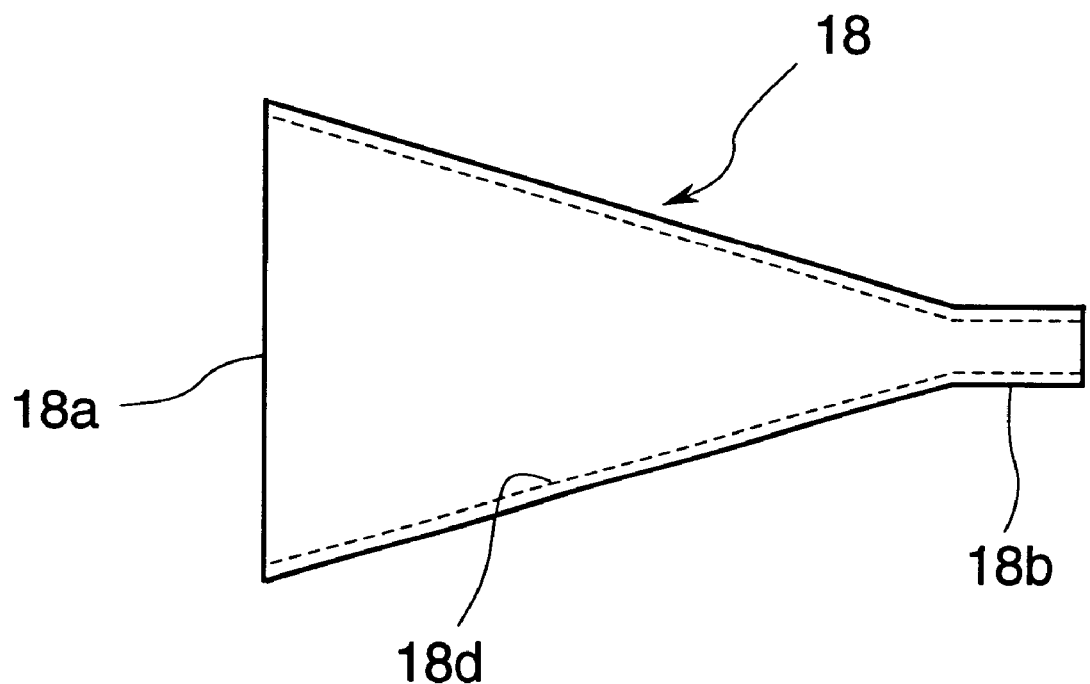
FIG. 8 is a side view showing a funneled tube, used in the embodiment.
Figure 17:
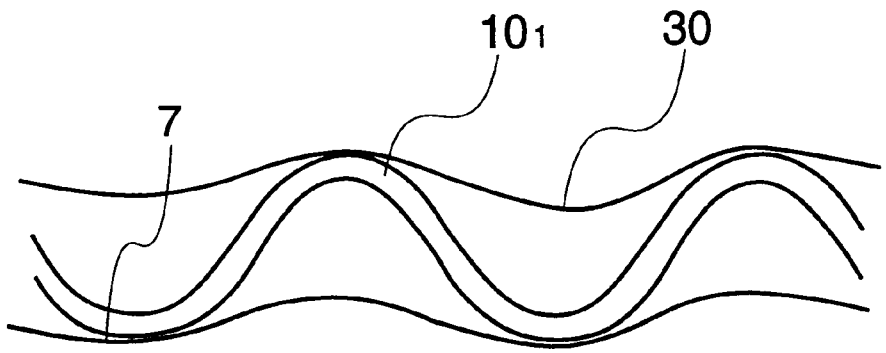
FIG. 17 is a schematic diagram showing a front end wire ring, a film member and a cover of the embodiment of the artificial blood vessel being folded.

A funneled tube 18 as a guide tube, as shown in FIG. 8, is provided to help collapse the artificial blood vessel A. The funneled tube 18 is provided with an enlarged inlet opening 18a of an enlarged diameter at the rear end portion, through which the tubular artificial blood vessel A is inserted into the funneled tube 18. The funneled tube 18 is gradually reduced in diameter from the enlarged inlet opening 18a to end in a tubular connector 18b of a smaller diameter at the front end portion thereof, so that the tube 18 has a tapered inner surface 18d. The funneled tube 18 is, as shown in FIG. 17, removably connected to the cartridge 6 by inserting the front connector 18b into the rear end portion 6b of the cartridge 6.

The process of collapsing the artificial blood vessel A and implanting it into a position to be implanted, namely, a target portion (an affected part 26 in FIG. 22) of a blood vessel 9 by means of the device B for transporting the artificial blood vessel and the device C for introducing the artificial blood vessel of the above-mentioned constructions, will now be described below.

Figure 9:
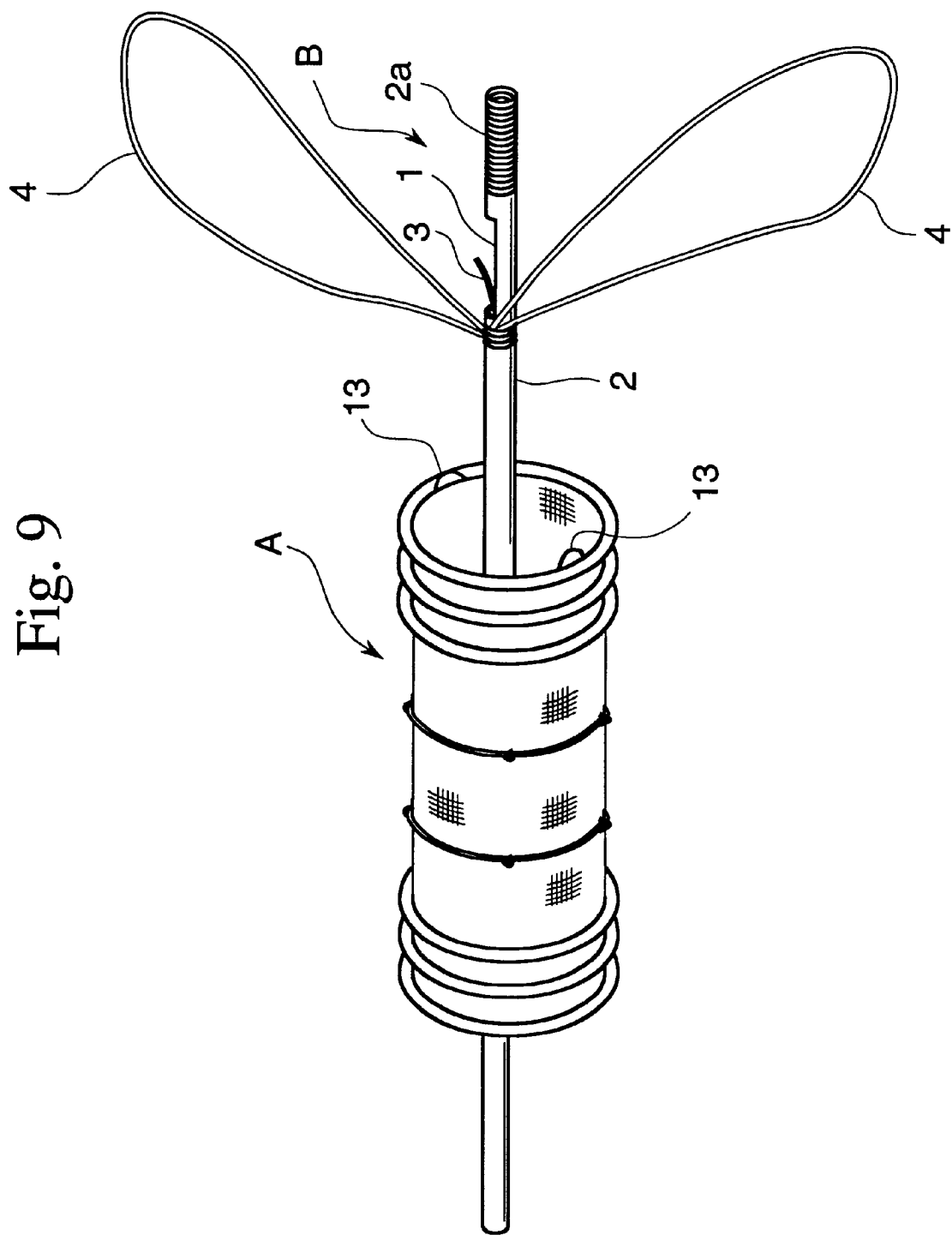
FIG. 9 is a perspective view of the artificial blood vessel through which the device for transporting the artificial blood vessel is loosely inserted.
Figure 10:
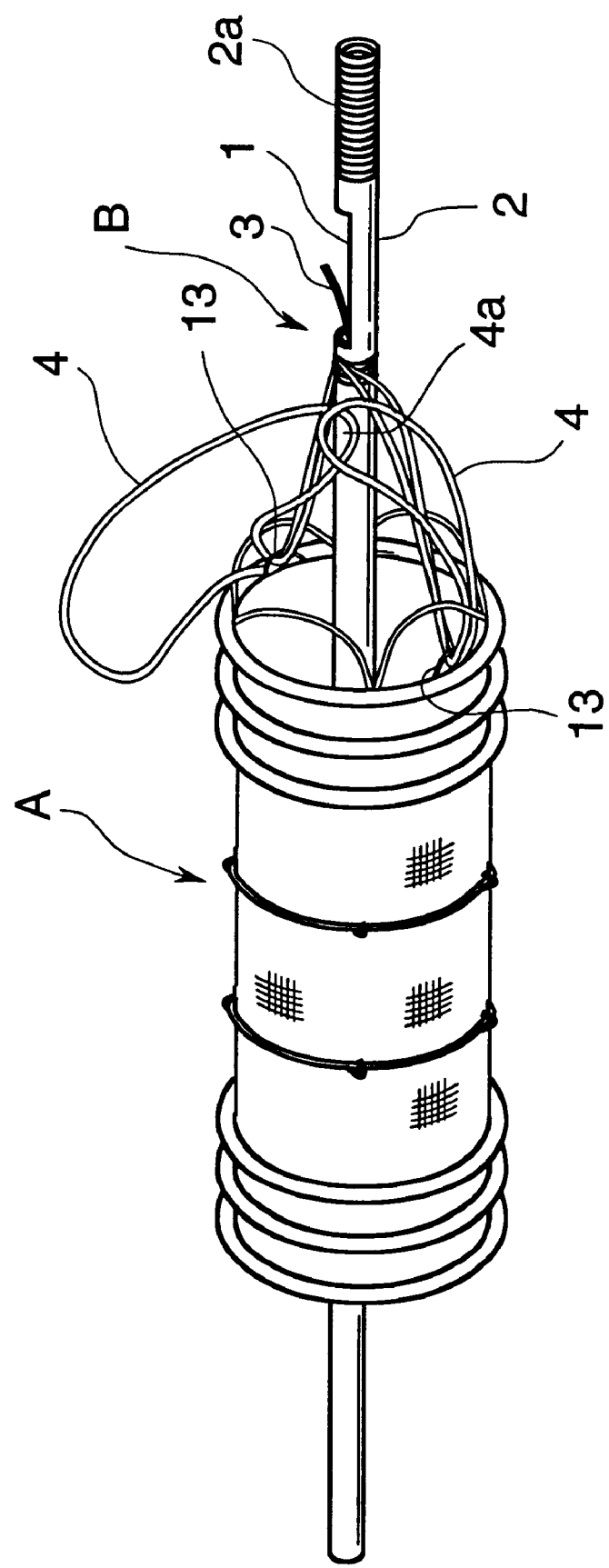
FIG. 10 is a perspective view showing a step to hold the artificial blood vessel by means of the device for transporting the artificial blood vessel.
Figure 11:
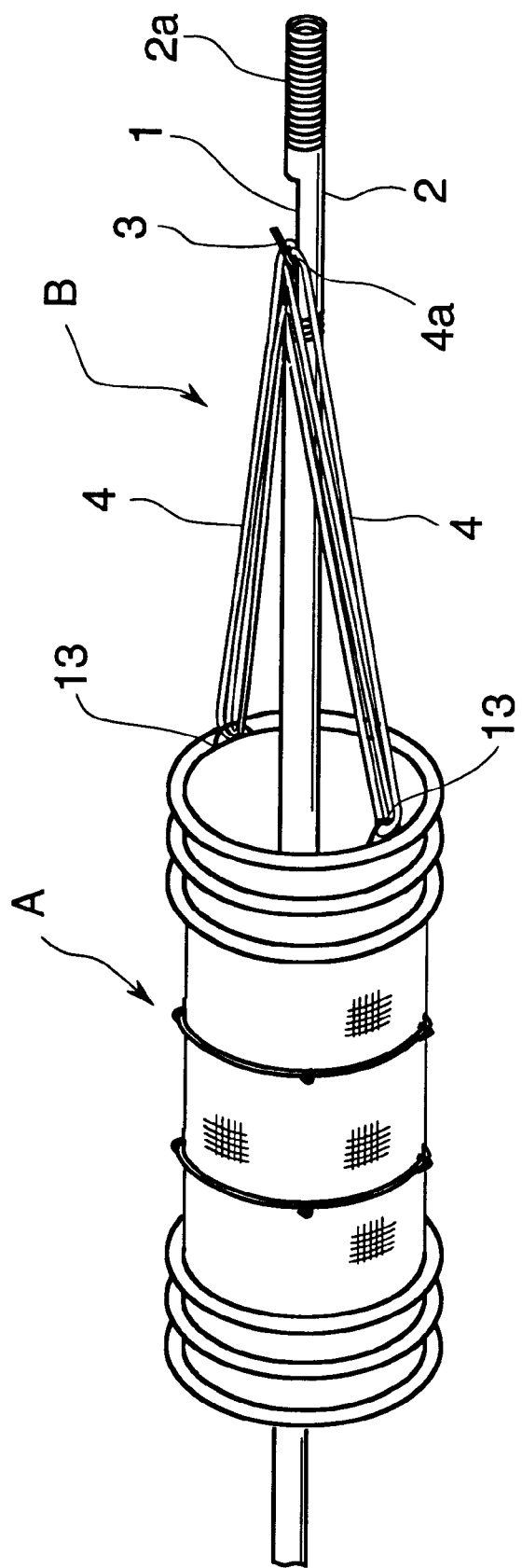
FIG. 11 is a perspective view showing a step to hold the artificial blood vessel by means of the device for transporting the artificial blood vessel.
Figure 12:
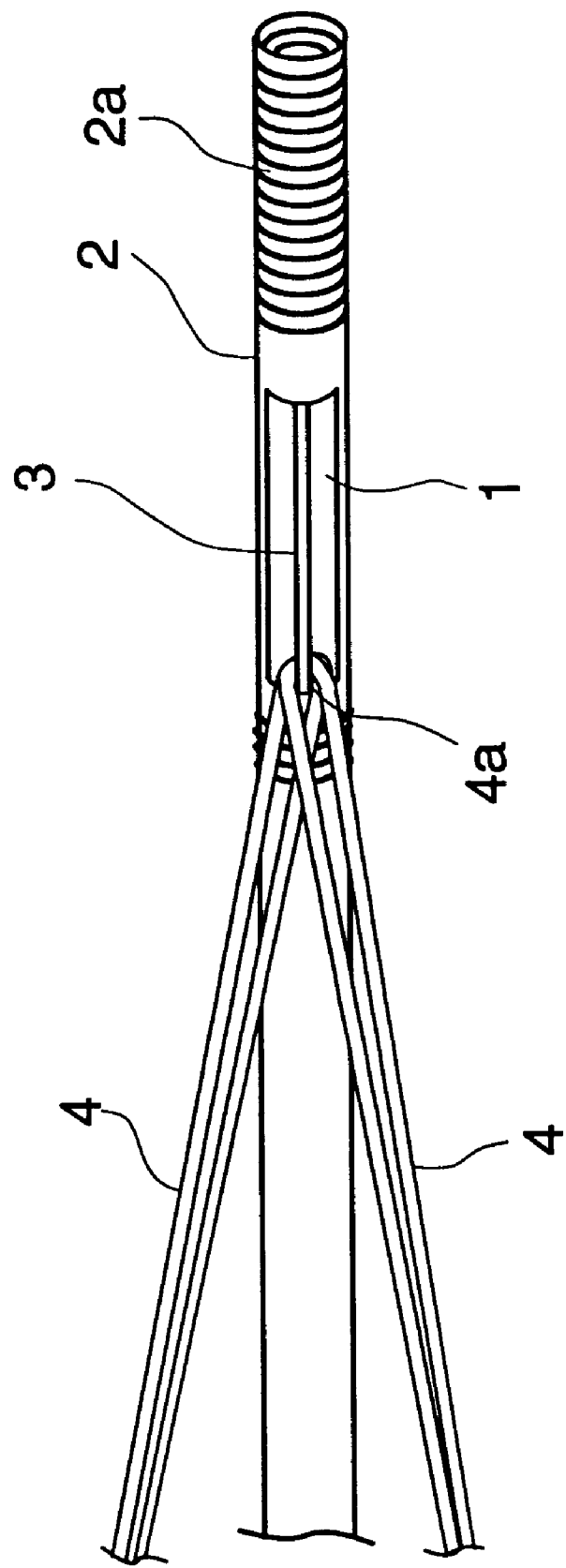
FIG. 12 is an enlarged perspective view showing part of the artificial blood vessel held by the device for transporting the artificial blood vessel.
Figure 13:
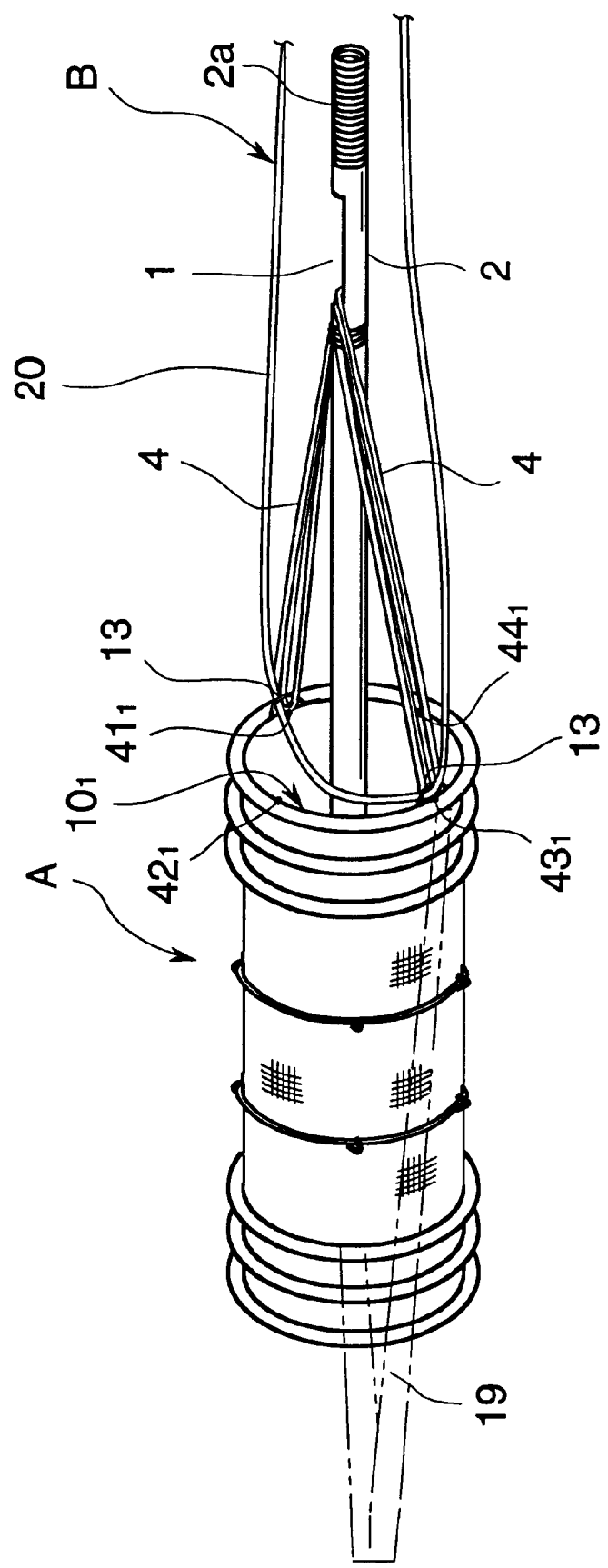
FIG. 13 is a perspective view showing a step to introduce the artificial blood vessel into a catheter.
Figure 14:
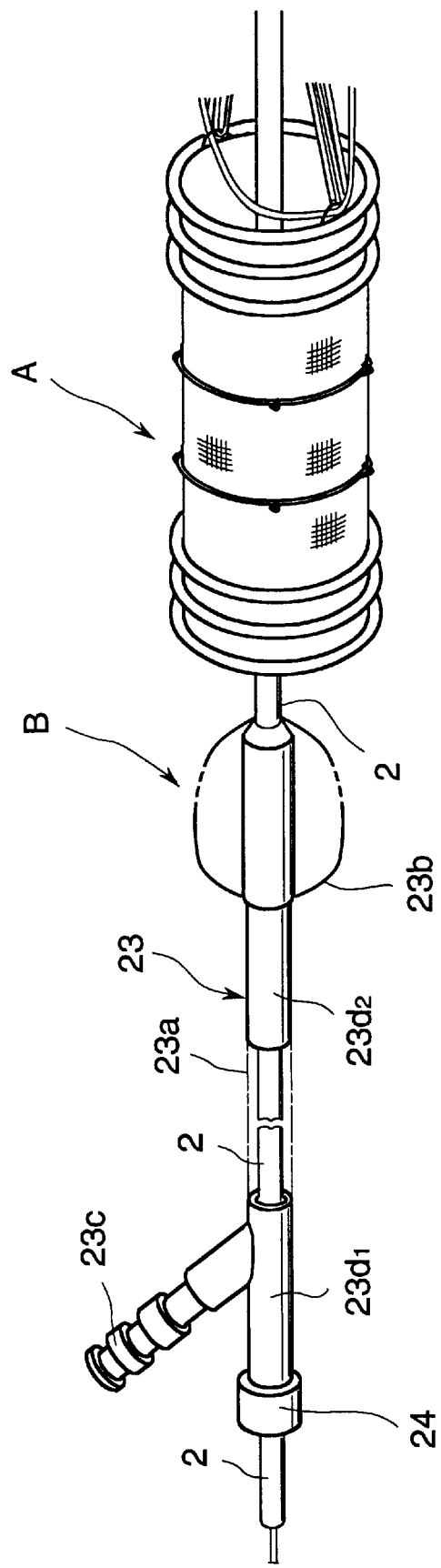
FIG. 14 is a perspective view showing a step to introduce the artificial blood vessel into the catheter.

First, the tube 2 of the device B for transporting the artificial blood vessel is inserted through the artificial blood vessel A as shown in FIG. 9, and each of a pair of strings 4 is passed through each hooking means 13 of the artificial blood vessel A as shown in FIG. 10, and the looped portions of the strings 4 overlap as shown at 4a. Next, a wire 3 has its forward end taken out of the side window 1 as shown in FIG. 11, and the overlapped portions of the looped portions 4a are hooked over the wire 3, and then the wire 3 has its forward end inserted again into the tube 2 through the side window 1 so as to hold the artificial blood vessel A on the wire 3 and the tube 2 through the strings 4 as shown in FIG. 12. Then, as shown in FIG. 13, the artificial blood vessel A is inserted into the cartridge 6 shown in FIG. 4 through the funneled tube 18 and with the forceps 19. In this embodiment the artificial blood vessel A is inserted into the cartridge 6 using the forceps 19, however, the artificial blood vessel A may be folded into an appropriate wavy shape and inserted into the cartridge 6 by hand without using any forceps. A concrete method for inserting the artificial blood vessel A using the forceps 19 will now be explained. First, the forceps 19 are put along the generatrices each of which passes through the dividing points $41_1$ and $43_1$ with a common front pull string 20 being passed through the front hooking means 13 provided at the dividing points $41_1$, $43_1$ on the front end wire ring $10_1$ of the artificial blood vessel A as shown in FIG. 13. Prior to this operation a balloon catheter 23, as shown in FIG. 14, may be attached to the tube 2, if necessary. The balloon catheter 23 comprises a pipe 23a, a balloon 23b formed on the front end portion of the pipe 23a, and an opening 23c provided in the rear end of the pipe 23a for air to be introduced into or taken out of the above-mentioned balloon 23b through the pipe 23a. The pipe 23a is loosely fitted over the tube 2 of the above-mentioned device B for transporting the artificial blood vessel. In other words, the rear end portion of the tube 2 of the device B for transporting the artificial blood vessel is drawn outside from the rear end of the balloon 23b of the balloon catheter 23 while the front end portion of the tube 2 is passed through the balloon 23b of the balloon catheter 23 and exposed outside, with the portions of the catheter 23 through which the tube 2 is passed being airtightly sealed. The rear end portion of the pipe 23a is removably connected to the tube 2 of the device B for transporting the artificial blood vessel by a fixing member 24, and the balloon catheter 23 and the tube 2 of the device B for transporting the artificial blood vessel can be moved together as a unit longitudinally when the fixing member 24 is fastened, and the balloon catheter 23 can be moved longitudinally relative to the tube 2 of the device B when the fixing member 24 is loosened. The balloon catheter 23 is so positioned that the front end thereof is spaced about 2 to 3 cm apart from the rear end of the artificial blood vessel A loosely fitted over the tube 2. Then the fixing member 24 on the balloon catheter 23 is fastened to fix the catheter 23 to the tube 2 so that the catheter 23 and the tube 2 can be moved together as a unit.

Figure 15:
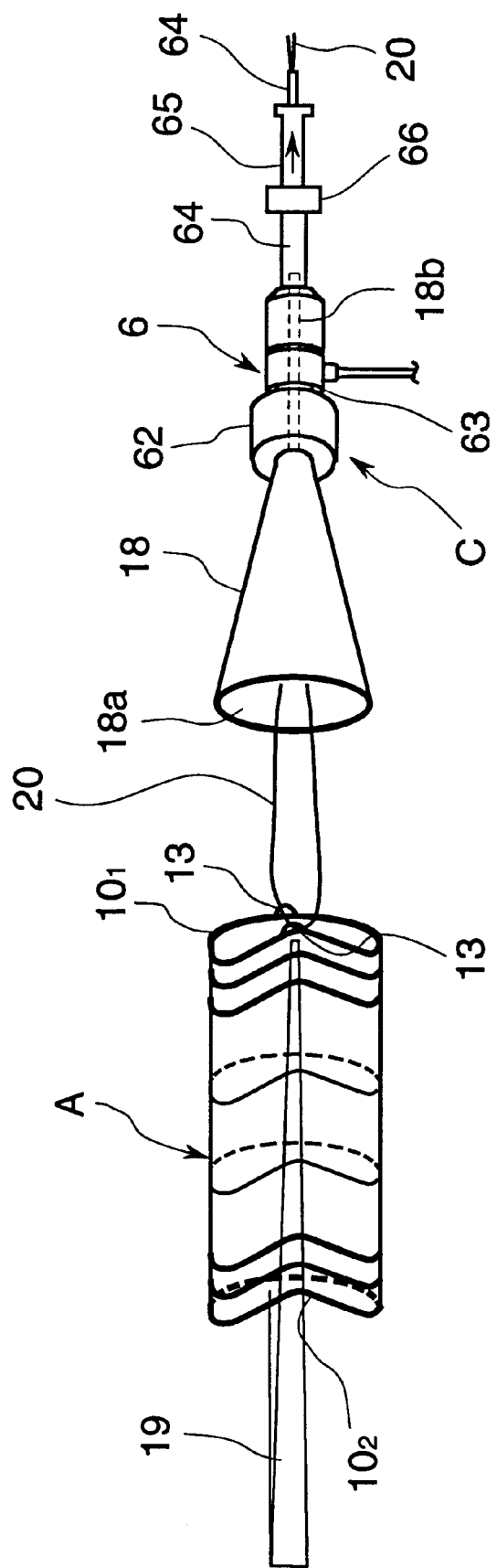
FIG. 15 is a perspective view showing a step to introduce the artificial blood vessel into the catheter by means of forceps.

Before or after the above step, the funneled tube 18 is attached to a cartridge 6 as shown in FIG. 15. In attaching the funneled tube 18 to the cartridge 6, the connector 18b of the funneled tube 18 is inserted into the annular member 62 of the cartridge 6 so that the check valve 68 of elastic membrane provided inside the annular member 62 is pushed open by the connector 18b of the funneled tube 18 as shown in FIG. 17, and the connector 18b is inserted a little deep into the straw 64 of the cartridge 6. Then the artificial blood vessel A is inserted into inside of the funneled tube 18 through the enlarged inlet opening 18a with picked by forceps as shown in FIG. 15.

Then the auxiliary front end wire ring $31_1$ of the artificial blood vessel A is deformed to be flat with the positions picked up by the forceps 19, namely the dividing points $41_1$, $43_1$ approaching toward each other to be pushed into the funneled tube 18 while the other dividing points $42_1$, $44_1$ restrained from the movement toward the tubular connector 18b by sliding contact with the tapered inner surface 18d of the funneled tube 18. When the auxiliary front end wire ring $31_1$ reaches adjacent the tubular connector 18b of the funneled tube 18, the auxiliary front end wire ring $31_1$ as a whole is folded into a regular wavy shape with the dividing points $41_1$, $43_1$ forming forwardly directed peaks and other dividing points $42_1$, $44_1$ forming the bottoms of forwardly directed valleys.

Figure 16:
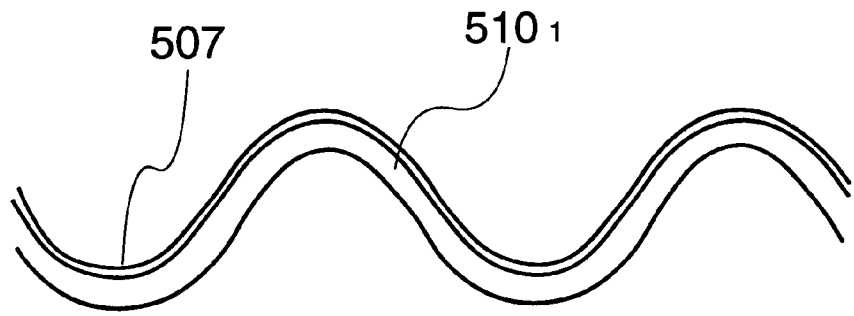
FIG. 16 is a schematic diagram showing a front end wire ring, a film member and a cover of a conventional artificial blood vessel being folded.

If a cover 507 is fixed to the front and rear end wire rings along the whole circumference thereof, the cover 507 tries to follow the movement of the wire ring $510_1$ completely as shown in FIG. 16. Then the cover 507 is folded into a shape whose long axis being shorter and wrinkles gather at a certain point, thereby to be bulky.

Figure 18:
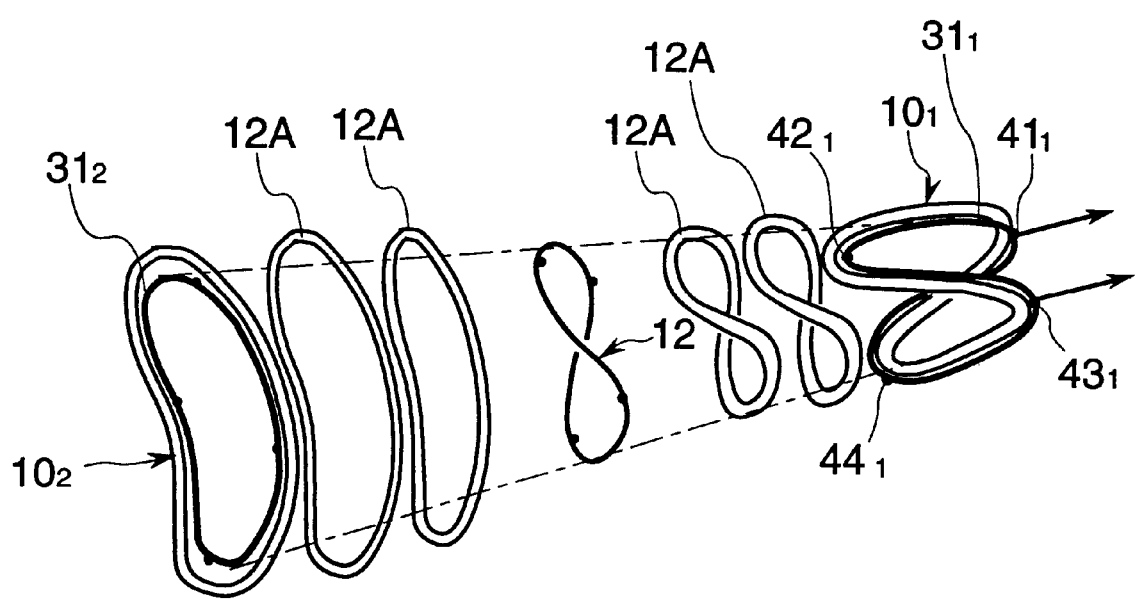
FIG. 18 is an explanatory view showing the artificial blood vessel being folded in a funneled tube.

In this embodiment, however, the front end wire ring $10_1$ can make a back and forth movement relative to the cover 7 within a certain range. Then the cover 7 does not have to follow the transformation of the front end wire ring $10_1$ completely as shown in FIG. 17. This helps a range of the cover 7 being folded into a small size compared with that of the front end wire ring $10_1$. Therefore, the cover 7 can be collapsed into small without forming almost any wrinkles at a position near the front end wire ring $10_1$ being folded. The front end wire ring $10_1$ can also move free from the cover 7 when folded, thereby to secure the front end wire ring $10_1$ a free movement with ease. The intermediate end wire rings 12A, the intermediate wire rings 12, the rear end wire ring $10_2$ and the auxiliary rear end wire ring $31_2$ also begin to transform into a wavy shape having the same phase as that of the auxiliary front end wire ring $31_1$, as shown in FIG. 18, because both of them follow the movement of the front end wire ring $10_1$ toward the tubular connector 18b with picked by forceps 19.

Figure 19:
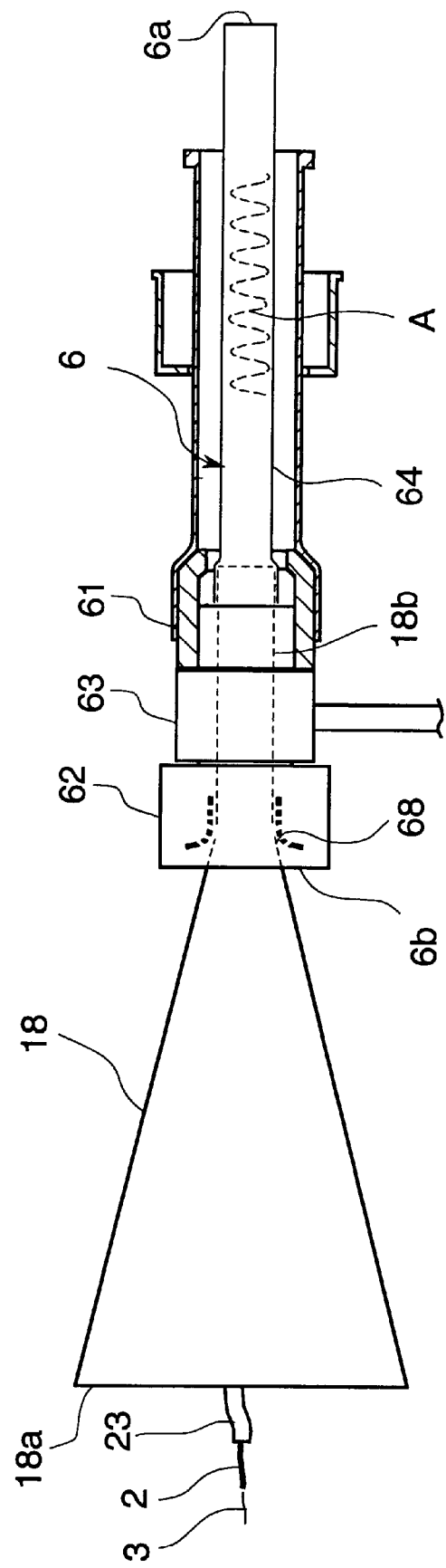
FIG. 19 is a partly cut-out side view showing the artificial blood vessel inserted into the cartridge.
Figure 20:
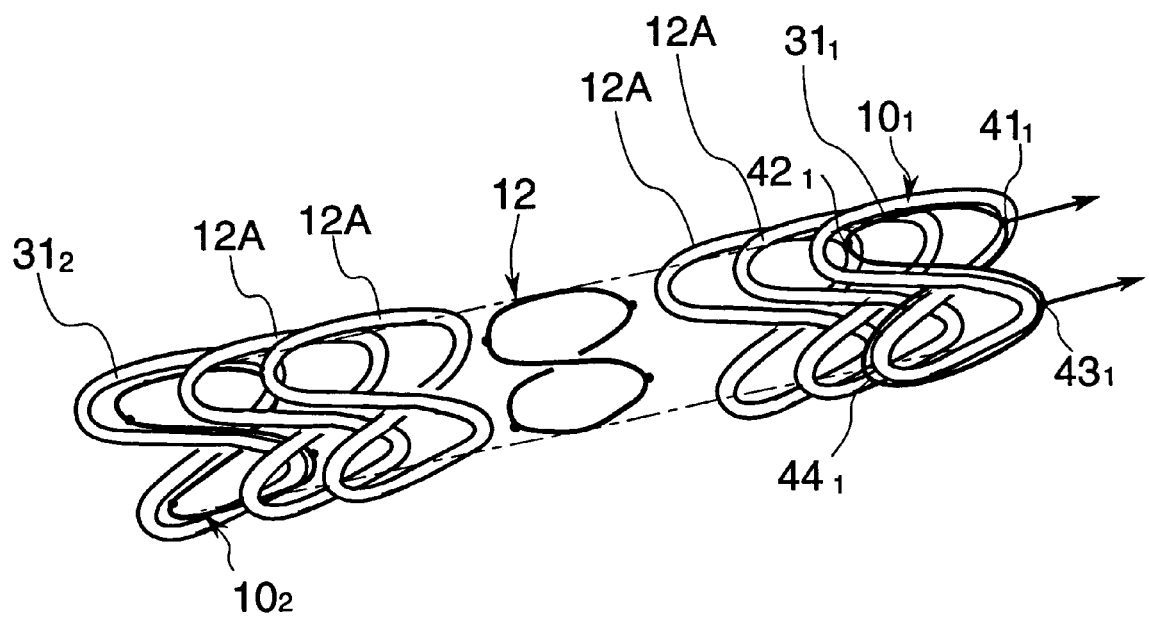
FIG. 20 is a schematic diagram showing each of the wire rings being folded.

Under this condition, the forceps 19 are withdrawn from the funneled tube 18 and the front pull string 20 is pulled forward to farther introduce the artificial blood vessel A into the cartridge 6. As the front pull string 20 is pulled forward, the pulling force applied to the auxiliary front end wire ring $31_1$ is transmitted through the tubular cover 7 to the intermediate end wire rings 12A, the intermediate wire rings 12, the auxiliary rear end wire ring $31_2$ and the rear end wire ring $10_2$, thereby to cause the intermediate end wire rings 12A, the intermediate wire rings 12, the auxiliary rear end wire ring $31_2$ and the rear end wire ring $10_2$ to follow the movement of the auxiliary front end wire ring $31_1$ and the front end wire ring $10_1$. With the artificial blood vessel A perfectly contained in a cartridge 6 as shown in FIG. 19, the intermediate end wire rings 12A, the intermediate wire rings 12, the auxiliary rear end wire ring $31_2$ and the rear end wire ring $10_2$ are collapsed into a small size to take a wavy shape having the same phase as that of the front end wire ring $10_1$ and the auxiliary front end wire ring $31_1$ as shown in FIG. 20.

At this time, the rear end wire ring $10_2$ and the intermediate end wire ring 12A can make a back and forth movement relative to the cover 7 within a certain range, like the front end wire ring $10_1$. Then the cover 7 does not have to follow the transformation of the wire rings $10_2$ and 12A completely. This helps a range of the cover 7 being folded small compared with the wire rings $10_2$ and 12A. Therefore, the cover 7 can be collapsed into small without forming almost any wrinkles at a position near the front end wire ring $10_2$, 12A being folded. The wire rings $10_2$ and 12A can also move free from the cover 7 when folded, thereby to secure the wire rings $10_2$ and 12A a free movement with ease.

Next, the front pull string 20 is untied or cut at an appropriate position thereof and pulled at its end so as to be withdrawn from the front hooking means 13, and the funneled tube 18 is withdrawn from the cartridge 6. Consequently, the artificial blood vessel A is contained in the straw 64 of the cartridge 6, as shown in FIG. 21, and only the balloon catheter 23 in which the tube 2 is provided is exposed outside through the rear end portion 6b of the cartridge 6 with the check valve 68 opened a little.

Figure 22:
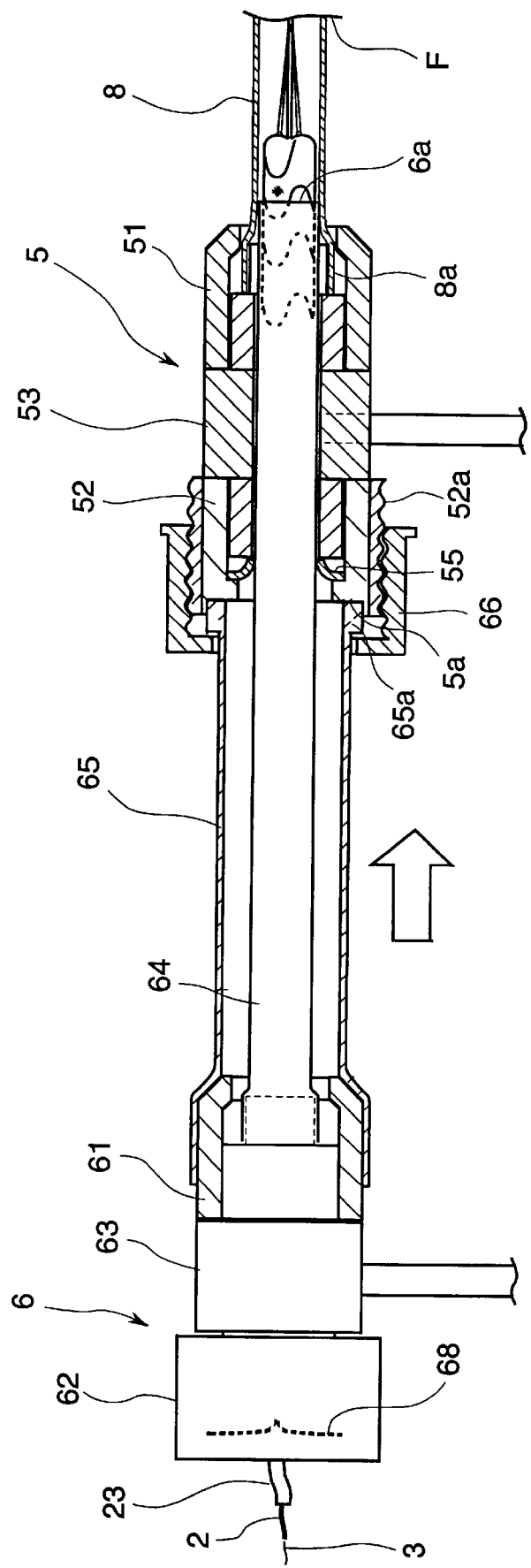
FIG. 22 is a partly cut-out side view showing the cartridge connected to the attachment.

On the other hand, the catheter 8 has been previously inserted through as shown in FIG. 22, for example, the coxal artery adjacent the groin F into the blood vessel 9 as far as the front end of the catheter 8 has been positioned a little beyond the affected portion 26 such as an aneurysm of the aorta as shown in FIG. 23. The attachment 5 connected to the open end 8a of the catheter 8 is, as shown in FIG. 22, exposed outside the body. Next, the straw 64 of the cartridge 6 into which the artificial blood vessel A has been inserted is pushed into the attachment 5 through the rear end portion 5a thereof until the large portion 65a makes abutting engagement with the rear end portion 5a with the check valve 5 opened as shown in FIG. 22 and the cap 66 is advanced to helically connect to the outer surface of the helical member 52a. Then the straw 64 of the cartridge 6 is positioned so that the front end 6a thereof is smoothly connected to the inner surface of the open end 8a of the catheter 8 and this condition is kept by the helical connection of the cap 66 and the helical member 52a. Under the condition, the balloon catheter 23 is gripped and the balloon catheter 23 is pushed so as to be inserted gradually deeply into the catheter 8. As the tube 2 is, as shown in FIG. 14, connected to the balloon catheter 23 through the fixing member 24 and the artificial blood vessel A is held by the tube 2, movement of the balloon catheter 23 causes the artificial blood vessel A to be transported gradually to the deep position in the body. The balloon catheter 23 is pushed until the front end of the tube 2 is positioned at the front end of the catheter 8, as shown in FIG. 23. At this time the artificial blood vessel A is positioned at the affected portion 26 as the target position. Then, as the catheter 8 is withdrawn as shown in FIG. 24, with the balloon catheter 23 and the tube 2 into which the wire 3 is inserted left at the objective position, the collapsed artificial blood vessel A in the catheter 8 is released at the affected portion 26 in the blood vessel 9 while expanding gradually from the front end as shown in FIGS. 24, 25 and 26. The released artificial blood vessel A is restored to its original tubular shape and urged against the inner wall of the blood vessel 9. In other words, when the artificial blood vessel A collapsed into small as shown in the figures is released from the catheter 23, each of the quadrisecting points elastically restores to a direction generally perpendicular to the blood vessel 9. Consequently, the artificial blood vessel A restores itself with each end portion thereof open and the internal space of the artificial blood vessel A is not closed by the internal wall of the blood vessel 9.

Especially in this embodiment, since the cover 7 is collapsed without forming a big wrinkle, the cover 7 restores to an original tube-shape quickly and easily with responding to each wire rings $10_1$, $10_2$ and 12A restoring to their original shape when released from the catheter.

Figure 33:
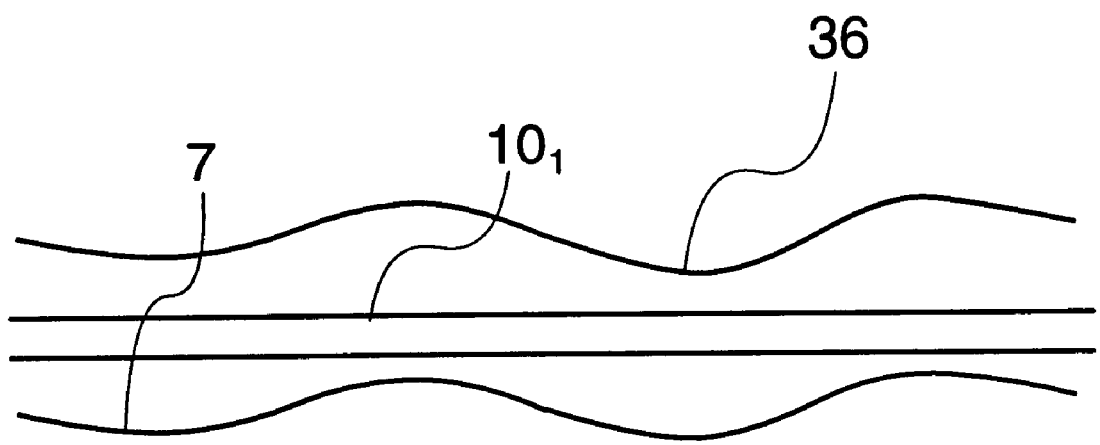
FIG. 33 is a further different modified form of the film member.

Then the fixing member 24 shown in FIG. 14 is loosened to disconnect the balloon catheter 23 from the tube 2, and the balloon catheter 23 is advanced along the tube 2 into the artificial blood vessel A with the tube 2 kept at the objective position as far as the front end of the balloon catheter 23 reaches the front end of the artificial blood vessel A as shown in FIG. 33, whereupon the balloon 23b is inflated by introducing air through the opening 23c as shown in FIG. 25 thereby to restore the artificial blood vessel A completely to its original shape and securely fix it onto the inner wall of the blood vessel. After the artificial blood vessel A has been thus fixed, the balloon 23b of the balloon catheter 23 is deflated by drawing air through the opening 23c and the balloon catheter 23 is pulled out from the artificial blood vessel A by pulling the pipe 23a rearwardly. Then it is confirmed that the artificial blood vessel A has been fixed onto the inner wall of the blood vessel 9, and then the wire 3 is pulled out of the tube 2. As the front end of the wire 3 passes the rear edge of the side window 1 of the tube 2 as shown in FIG. 10, the loop portion 4a of the string 4 that has been caught by the wire 3 at the side window 1 is released from the wire 3. Under the condition, when the tube 2 is pulled out, the string 4 slips out of the front hooking means 13 of the artificial blood vessel A. The balloon catheter 23 and the tube 2 are then connected again by the fastener 24 and pulled out of the human body with only the artificial blood vessel A left at the desired position in the blood vessel 9.

As mentioned above, in accordance with the invention, the artificial blood vessel A is implanted into the affected portion 26, and restored to its original shape, thereby to effectively prevent occlusion of the affected portion 26 in the blood vessel 9. With the above-mentioned artificial blood vessel A and its collapsing method, the artificial blood vessel A can be collapsed with ease and accuracy.

Especially, in this embodiment since the front and rear end wire rings $10_1$, $10_2$ and intermediate end wire wing 12A are fixed to the cover 7 so as to allow a back and forth movement relative to the cover 7, it can be prevented that a big wrinkle is formed in a cover 7 when collapsed into small, thereby to fold the artificial blood vessel A smoothly and to restore the artificial blood vessel A in a body smoothly. This contributes to an improved condition of implanting the artificial blood vessel A. In addition, since the annular gap formed between each of the wire rings $10_1$, $10_2$ and 12A and the cover 7 is liquidtightly sealed, the artificial blood vessel A produces an improved sealing effect on the front and rear end thereof, thereby to effectively prevent the blood leakage from the annular gap between the wire rings $10_1$, $10_2$ and 12A and the cover 7. Further, since each of the wire rings $10_1$, $10_2$ and 12A can move freely to the cover 7 as shown in FIG. 28, each of the wire rings $10_1$, $10_2$ and 12A gets a little influence from the cover 7 and tightly attaches to the inner wall of the affected blood vessel, thereby to improve a seal effect. This improves a condition of implanting the artificial blood vessel A by preventing blood flowing into an aneurysm, which will surely lead to a high successful rate of implantation.

In addition, since the front and rear end auxiliary wire rings $31_1$, $31_2$ are arranged on the front and rear end 7a, 7b of the cover 7, they can help the artificial blood vessel A attach tightly to the inner wall of the affected blood vessel with cooperation with the front and rear end wire rings $10_1$, $10_2$ when released from the catheter, thereby to improve attachability of the artificial blood vessel A to a human body.

The present claimed invention is not limited to the embodiment described above.

Figure 29:
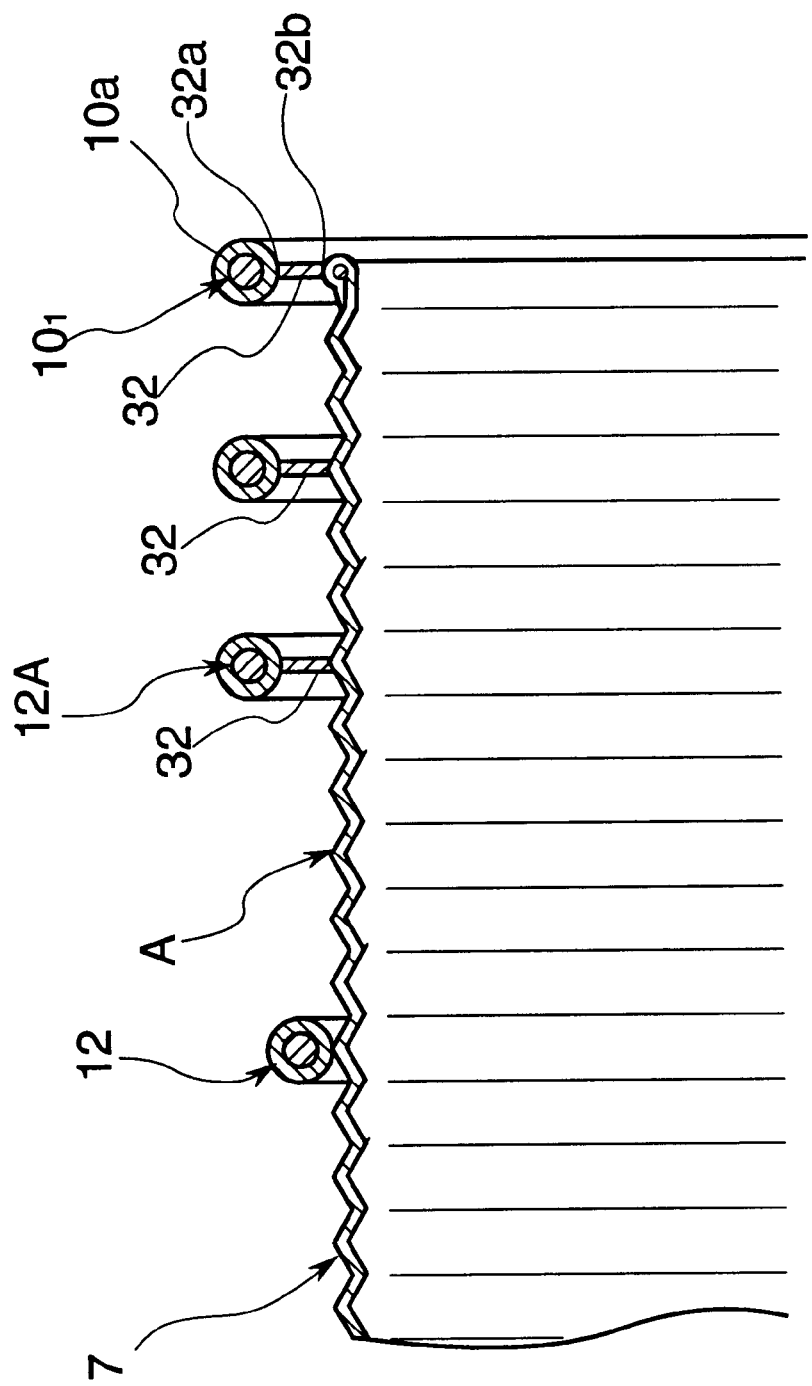
FIG. 29 is a modified form of the film member in accordance with the invention.
Figure 30:
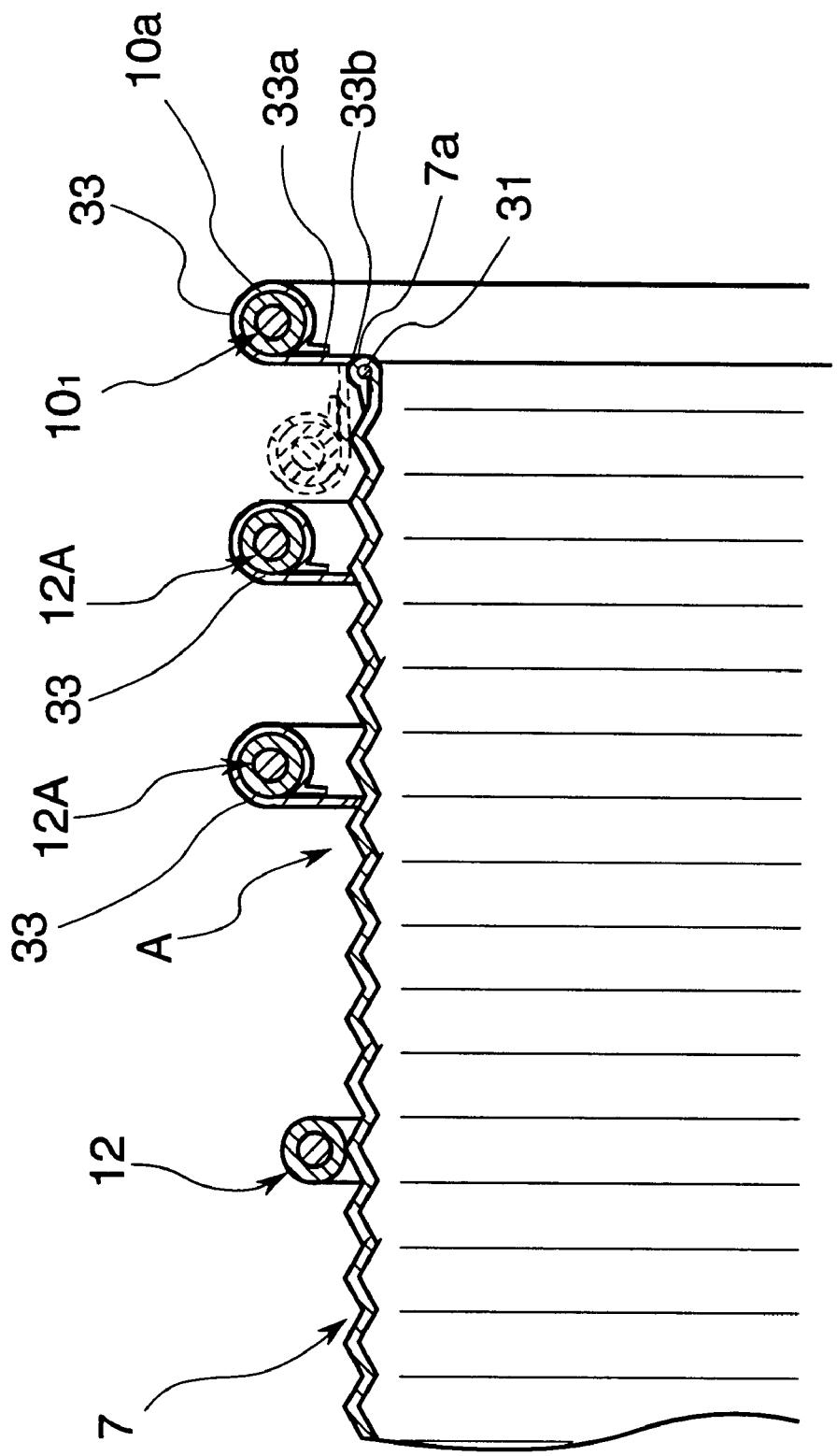
FIG. 30 is another modified form of the film member.

For example, as shown in FIG. 29, the film member 32 may be an annular film. Each of the front and rear end wire rings $10_1$, $10_2$ and intermediate end wire rings 12A is respectively attached to the film member 32 at positions which almost surround the outer circumferential end 32a of the film member 32, and the inner circumferential end 32b of the film member 32 is attached to the cover 7 at positions which almost surround the outer circumference of the cover 7. In this case the film member 32 allows each of the wire rings $10_1$, $10_2$ and 12A to make a back and forth movement relative to the cover 7 by making use of the transformation of the film member 32. The film member 33, as shown in FIG. 30, may be annular, in which case, the film member 33 wraps each of the front and rear end wire rings $10_1$, $10_2$ and intermediate end wire rings 12A at almost all the outer circumferential end 33a thereof and the inner circumferential end 33b of the film member 33 is attached to the cover 7 at positions which almost surround the outer circumference of the cover 7. In this case the film member 33 allows each of the wire rings $10_1$, $10_2$ and 12A to make a back and forth movement relative to the cover 7 by making use of the transformation of the film member 33.

Figure 31:
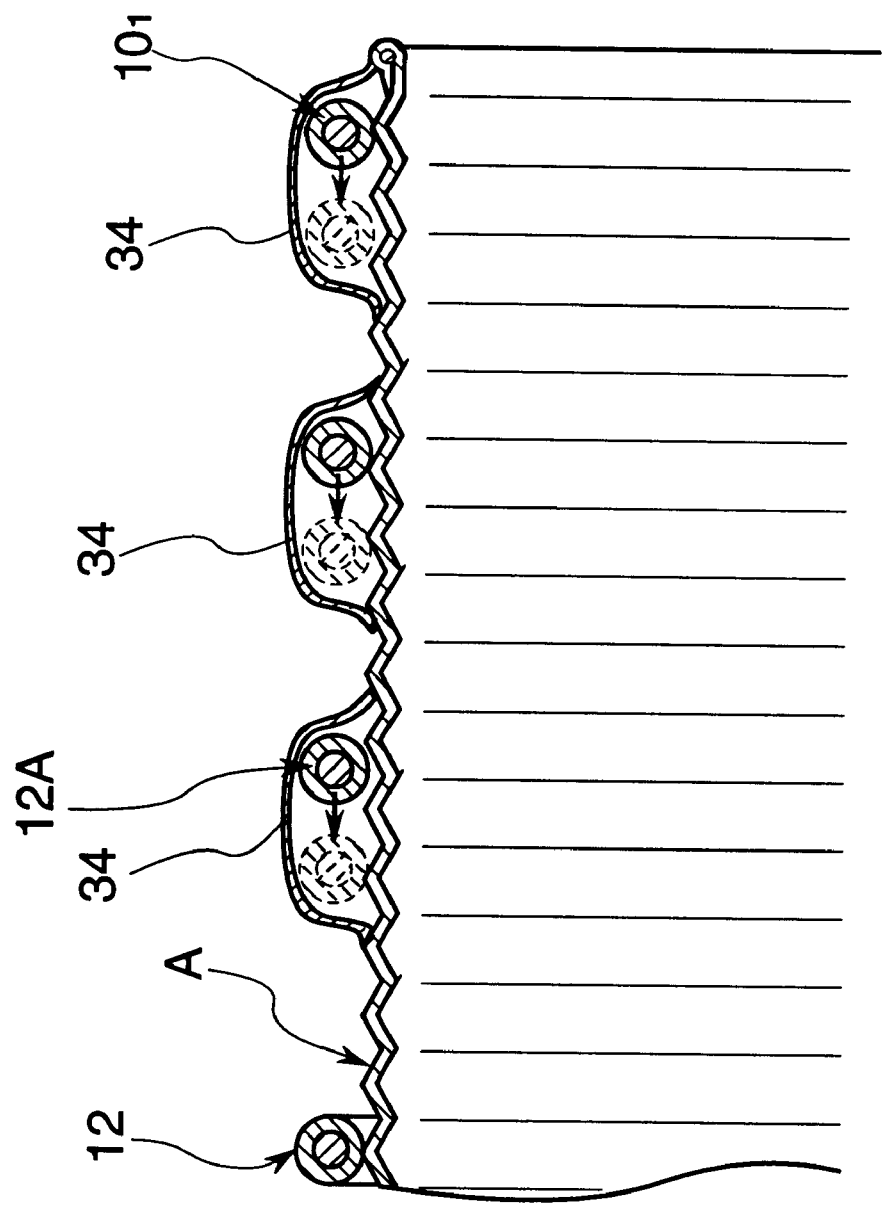
FIG. 31 is a further different modified form of the film member.
Figure 32:
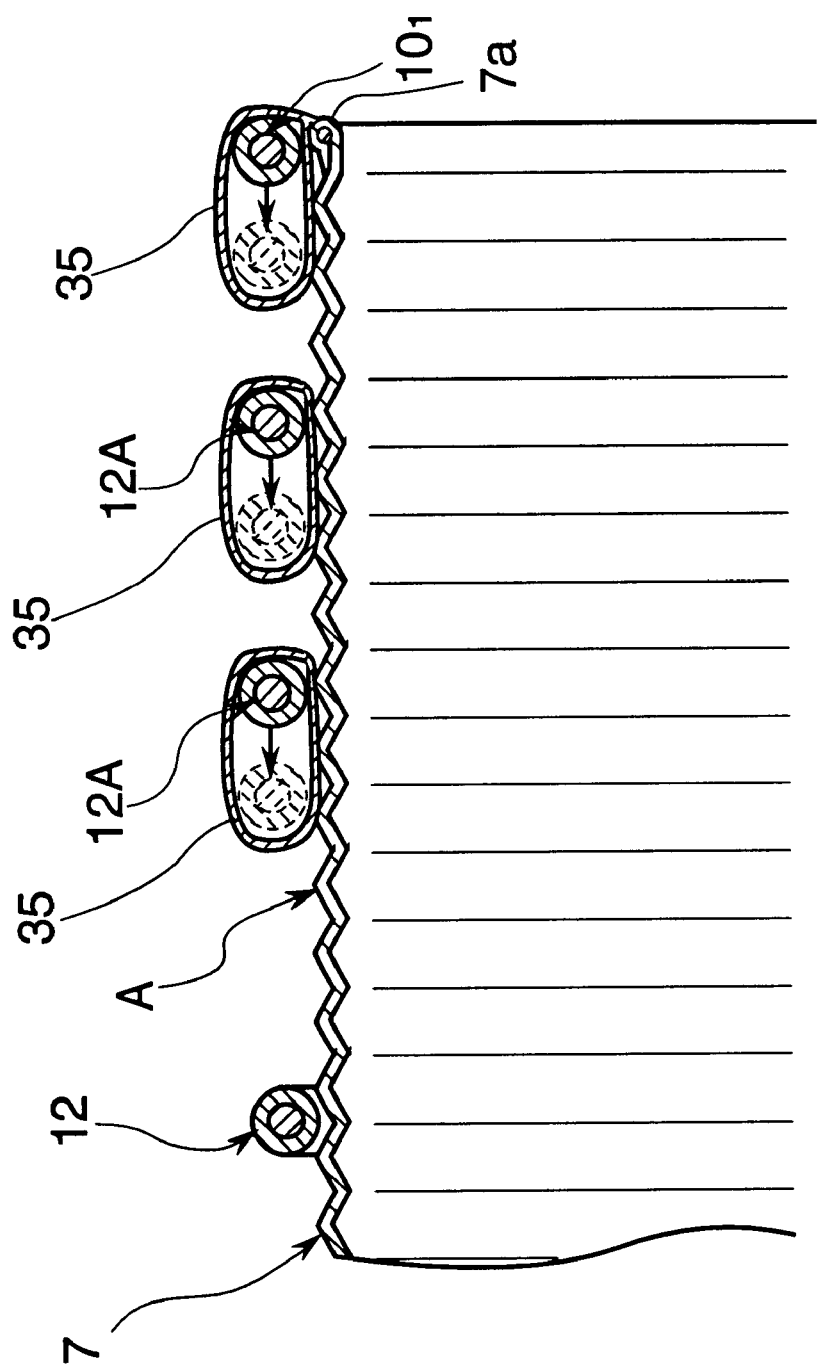
FIG. 32 is another different modified form of the film member.

The film member 34, as shown in FIG. 31, may form a space between the cover 7 and itself and in the space each of the front and rear end wire rings $10_1$, $10_2$ and the intermediate end wire ring 12A is wrapped and each of the wire rings $10_1$, $10_2$ and 12A can make a back and forth movement relative to the cover 7. The film member 35, as shown in FIG. 32, may have a long and narrow space therein along the direction of back and forth in which each of the wire rings $10_1$, $10_2$ and 12A is wrapped so as to allow a back and forth movement relative to the cover 7.

With these arrangements, the same effects can be obtained as that of the above-described embodiment.

Further, as shown in FIG. 33, the film member 36 and the cover 7 may have a wavy shape undulating along the circumference of the film member 36 and the cover 7 with a peak facing a peak of the wire rings and a valley facing a valley of the wire rings when the wire rings are folded into a wavy shape. With the arrangement, since a margin for folding each of the wire rings can be made bigger, a range of movement of the cover 7 can be made smaller. As a result, it can effectively prevent the cover 7 from bringing about wrinkles, thereby to secure an improved folding movement and restoration of the artificial blood vessel A.

In addition if the above film members 30, 32, 33, 34, 35 and 36 are made of an elastic fiber, the cover 7 can more effectively be prevented from causing wrinkles when collapsed into small.

Super absorbing processed polymer as an expanding element which expands itself when absorbing liquid may be filled in a space formed between each of the wire rings $10_1$, $10_2$, 12A and the film member 30, 32, 33, 34, 35 or 36. If blood flows into a bag-shaped film member 30, 32, 33, 34, 35 or 36 when the artificial blood vessel is collapsed into small, inserted into a body and released in the body, the expanding element expands itself in the bag-shaped film member 30, 32, 33, 34, 35 or 36. Then the film member 30, 32, 33, 34, 35 or 36 tightly attaches to the inner wall of blood vessel, thereby to improve a sealing effect of the artificial blood vessel A. An embodiment of the super absorbing processed polymer may be represented by a fiber of the super absorbing processed polymer which winds around the outer surface of each of the wire rings $10_1$, $10_2$, 12A, or a powder of the super absorbing processed polymer filled in a space formed between each of the film member 30, 32, 33, 34, 35 or 36 and each of the wire rings $10_1$, $10_2$ and 12A.

Further, if the front and rear end wire rings $10_1$, $10_2$ and the intermediate end wire ring 12A completely float in a bag-shaped film member 30, 34 or 35, a force to restore to its original shape may not be transferred appropriately to the wire rings $10_1$, $10_2$, 12A. In such a case, each of the wire rings $10_1$, $10_2$, 12A is preferably fixed to the cover intermittently by a string or something like that.

In the above embodiment, the circumferences of the front and rear end wire rings $10_1$, $10_2$ and the intermediate end wire ring 12A are covered with protective braid members 10a, however, it is a matter of course that the wire rings $10_1$, $10_2$ and 12A without any protective members such as braid members 10a can be wrapped in a film member.

In the above embodiment, the intermediate wire rings 12 are fixedly attached to the cover 7 by suturing or with adhesive intermittently at 4 points, however, midpoints between each of the adjacent points may be restricted from moving by an elastic or a longish string so that the intermediate wire rings 12 are fixed at 8 points or 16 points. As mentioned above, the intermediate wire ring 12 is fixedly attached to the cover 7 at the midpoints between each of the adjacent points with a certain free movement being secured for the intermediate wire ring 12. Since the intermediate wire ring 12 is free from dragging resistance from the cover 7, the free movement is secured for the intermediate wire ring 12 when collapsed and it can be prevented from being bent at an inappropriate position, thereby to fold the artificial blood vessel A into an appropriate wavy shape. Instead of this arrangement, it is also effective that the intermediate wire ring 12 is fixedly attached to the cover 7 at the points which is displaced to a direction to be folded.

Further, although not shown in drawings, the intermediate wire ring 12 may be wrapped in a mesh member, which is attached to surround almost all of the circumference of the cover 7. In accordance with the arrangement, the intermediate wire ring 12 is free from dragging resistance from the cover 7, the free movement is secured for the intermediate wire ring 12 so as to be collapsed with ease and it can be prevented from being bent at an inappropriate position.

Figure 34:
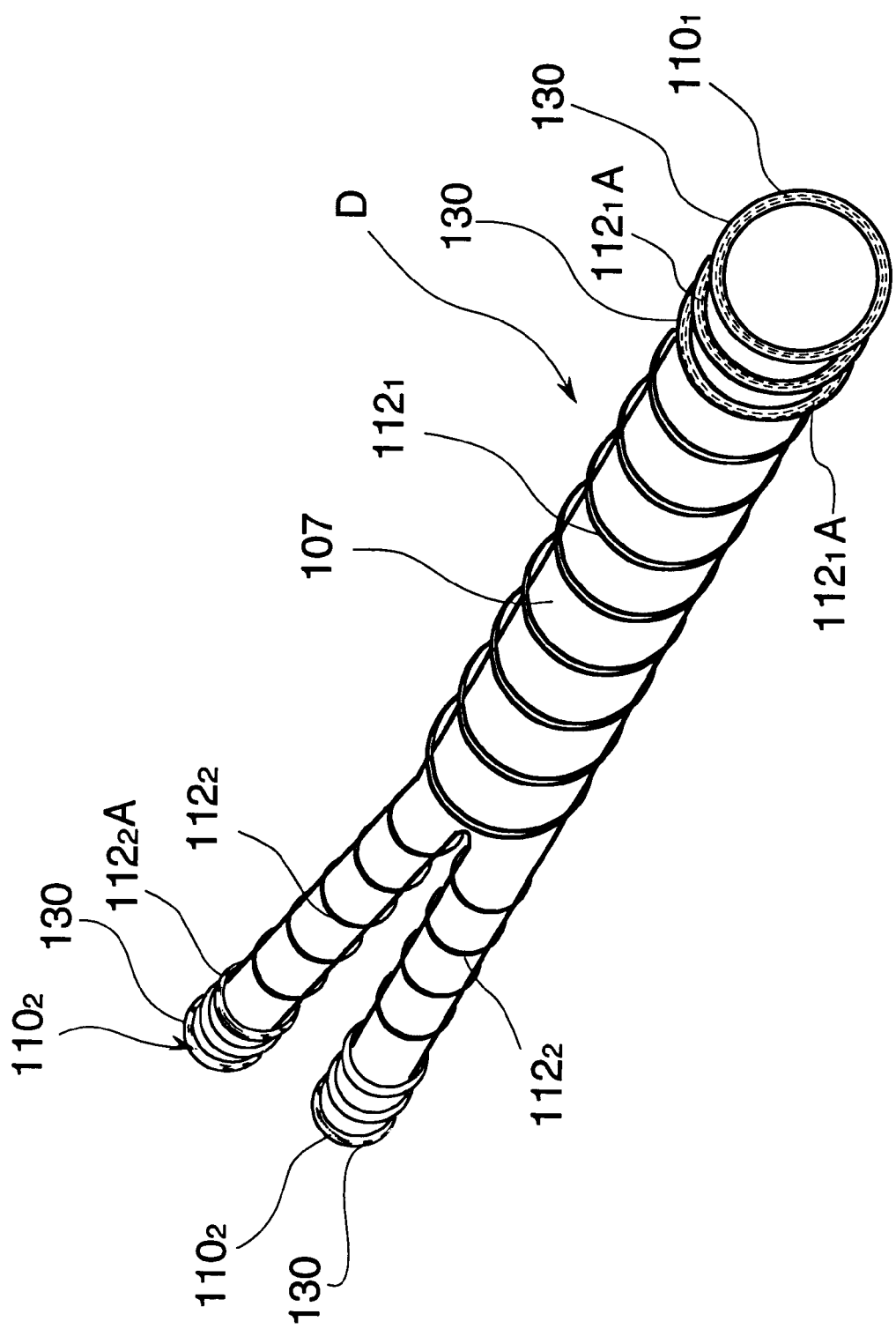
FIG. 34 is a perspective view of an artificial blood vessel showing another embodiment of the invention.

This invention is not limited to the above-mentioned embodiments. For example, if the vessel of the affected portion where the artificial blood vessel is to be implanted is different from the above mentioned and bifurcated, it is effective to use the artificial blood vessel D shown in FIG. 34. The artificial blood vessel D is to be implanted, for example, into the blood vessel of the groin. The artificial blood vessel D has fundamentally the same arrangement as that of the above-mentioned embodiment. This artificial blood vessel D, however, is for fitting the shape of the blood vessel into which the artificial blood vessel D is to be implanted and is characterized by that a single front end wire ring $110_1$ is arranged to face to two rear end wire rings $110_2$ arranged in parallel and each of whose diameter is smaller than that of the front end wire rings $110_1$, and a bifurcated tubular cover 107 connects the front end wire rings $110_1$ and two rear end wire rings $110_2$. And intermediate wire rings $112_1$ each of whose diameter is generally the same as that of the front end wire rings $110_1$ are arranged at the position whose diameter is the same as that of the front end wire ring $110_1$, while intermediate wire rings $112_2$ each of whose diameter is generally the same as that of the rear end wire ring $110_2$ are arranged at the position whose diameter is the same as that of the rear end wire ring $110_2$. Each of the intermediate wire rings $112_1$, $112_2$ is fixed to the cover 107 at a plurality of separate positions on the circumference thereof as the same as in the former embodiment. In the above bifurcated artificial blood vessel D, like the artificial blood vessel A of the former embodiment, if each of the single front end wire ring $110_1$, two of the intermediate wire rings $112_1$A arranged near the front end wire rings $110_1$, two rear end wire rings $110_2$ and two of the intermediate wire rings 12 arranged between the intermediate end wire rings $112_2$A is connected to the cover 7 through a film member 130 so that each of the wire rings $110_1$, $112_1$A, $110_2$, $112_2$A can make a back and forth movement relative to the cover 7 and that annular gaps between the wire rings $110_1$, $112_1A$, $110_2$, $112_2A$ and the cover 7 can liquidtightly be sealed, the same effect as that of the above-mentioned artificial blood vessel A can be obtained.

Figure 35:
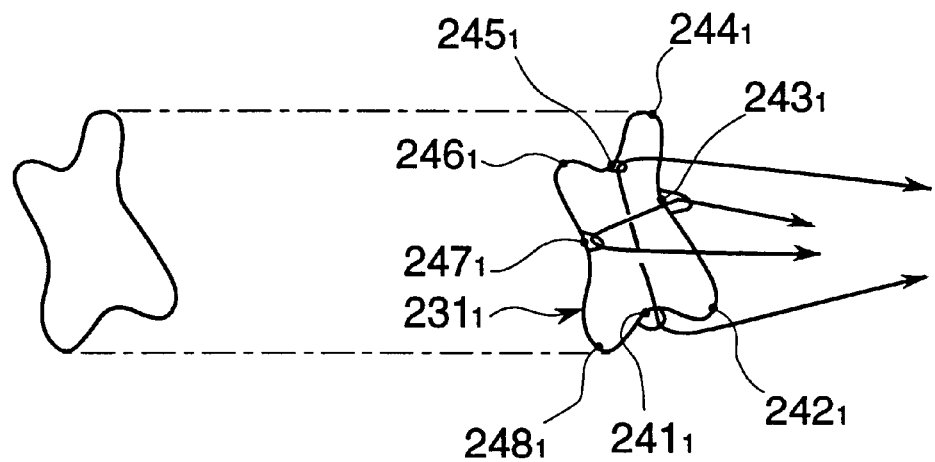
FIG. 35 is a diagram showing an artificial blood vessel in accordance with a different embodiment of the invention.
Figure 36:
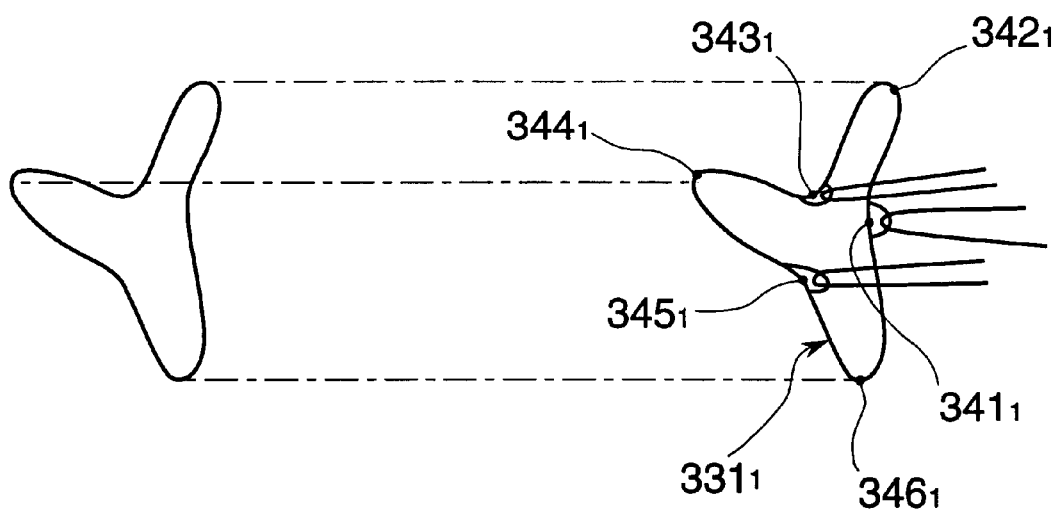
FIG. 36 is a diagram showing an artificial blood vessel in accordance with a further different embodiment of the invention.

This invention is not limited to the above-mentioned embodiments. For example, in the above embodiment, the auxiliary front end wire ring $31_1$ has its circumference divided into four equal arcs to set four dividing points. As shown in FIG. 35, an auxiliary front end wire ring $231_1$ may have its circumference divided into eight arcs to set eight dividing points $241_1$, $242_1$, $243_1$, $244_1$, $245_1$, $246_1$, $247_1$, $248_1$, four of which $241_1$, $243_1$, $245_1$, $247_1$ are provided with a hooking means and other four $242_1$, $244_1$, $246_1$, $248_1$ are not provided with a hooking means. As shown in FIG. 36, an auxiliary front end wire ring $331_1$ may have its circumference divided into six arcs to set sic dividing points $341_1$, $342_1$, $343_1$, $344_1$, $345_1$, $346_1$, three of which $341_1$, $343_1$, $345_1$ are provided with a hooking means and other three $342_1$, $344_1$, $346_1$ are not provided with a hooking means.

Figure 37:
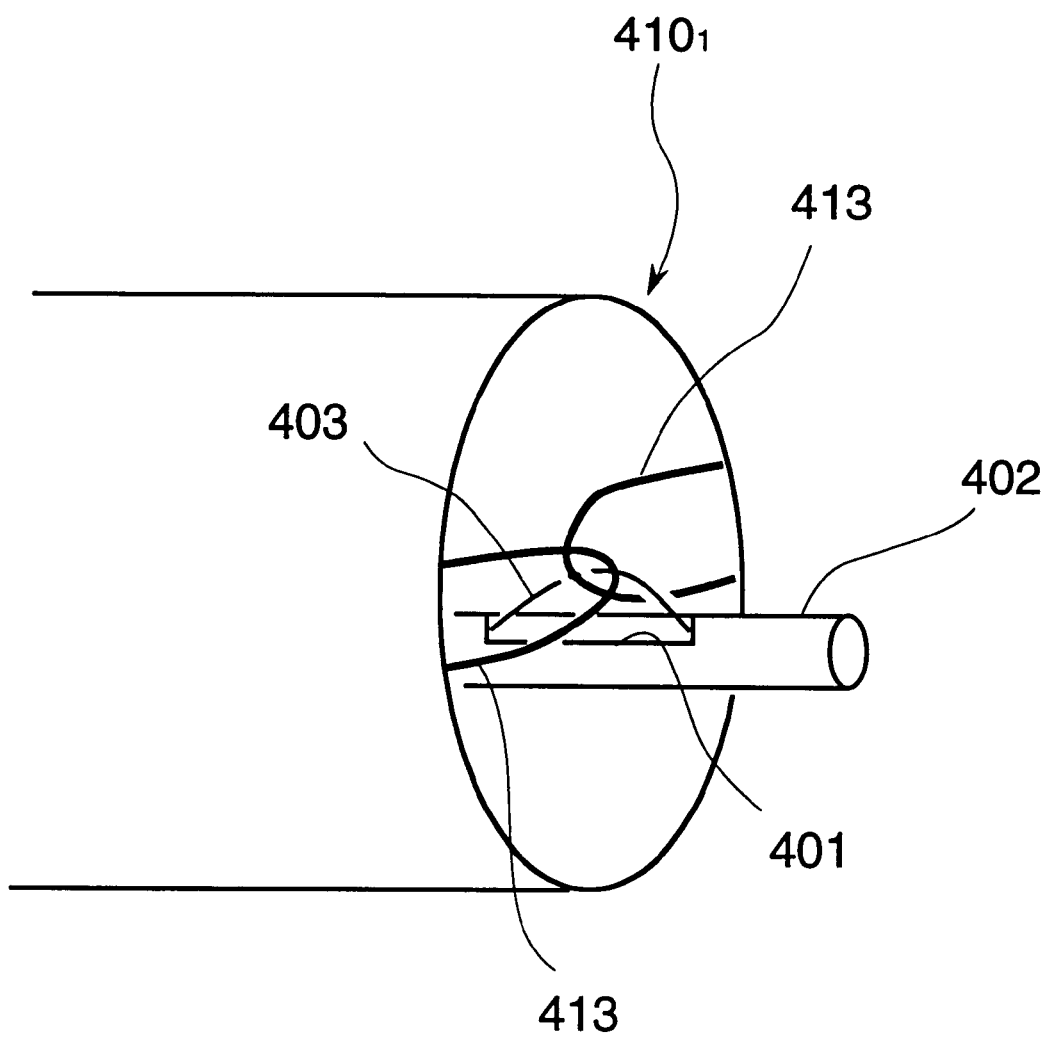
FIG. 37 is a perspective view showing a device for transporting the artificial blood vessel in accordance with a further different embodiment of the invention.

In the above embodiment, the device for transporting the artificial blood vessel is provided with a pair of strings having loop portions. The strings are not always to be provided in a pair. The strings provided in a pair, however, are effective because a balanced pulling force can be applied to the artificial blood vessel. The loop portions may be twisted as a whole. A device for transporting the artificial blood vessel comprising only a tube and a wire and which is not provided with strings may be used. For example, as shown in FIG. 37, front hooking means 413 formed on the front end wire ring $410_1$ are made a little longer, each of loop portions of the front hooking means 413 are overlapped, and a wire 403 pulled out of a side window 401 of a tube 402 is passed though and inserted into the overlapped loop portion so as to keep the artificial blood vessel. If there is no trouble to form holes directly on the tubular cover, it is also possible to keep the artificial blood vessel by means of a wire and a tube with making use of the holes as a hooking means.

Therefore, such a device for transporting the artificial blood vessel can be used to a patch to close a hole formed on a heart or the like.

Figure 38:
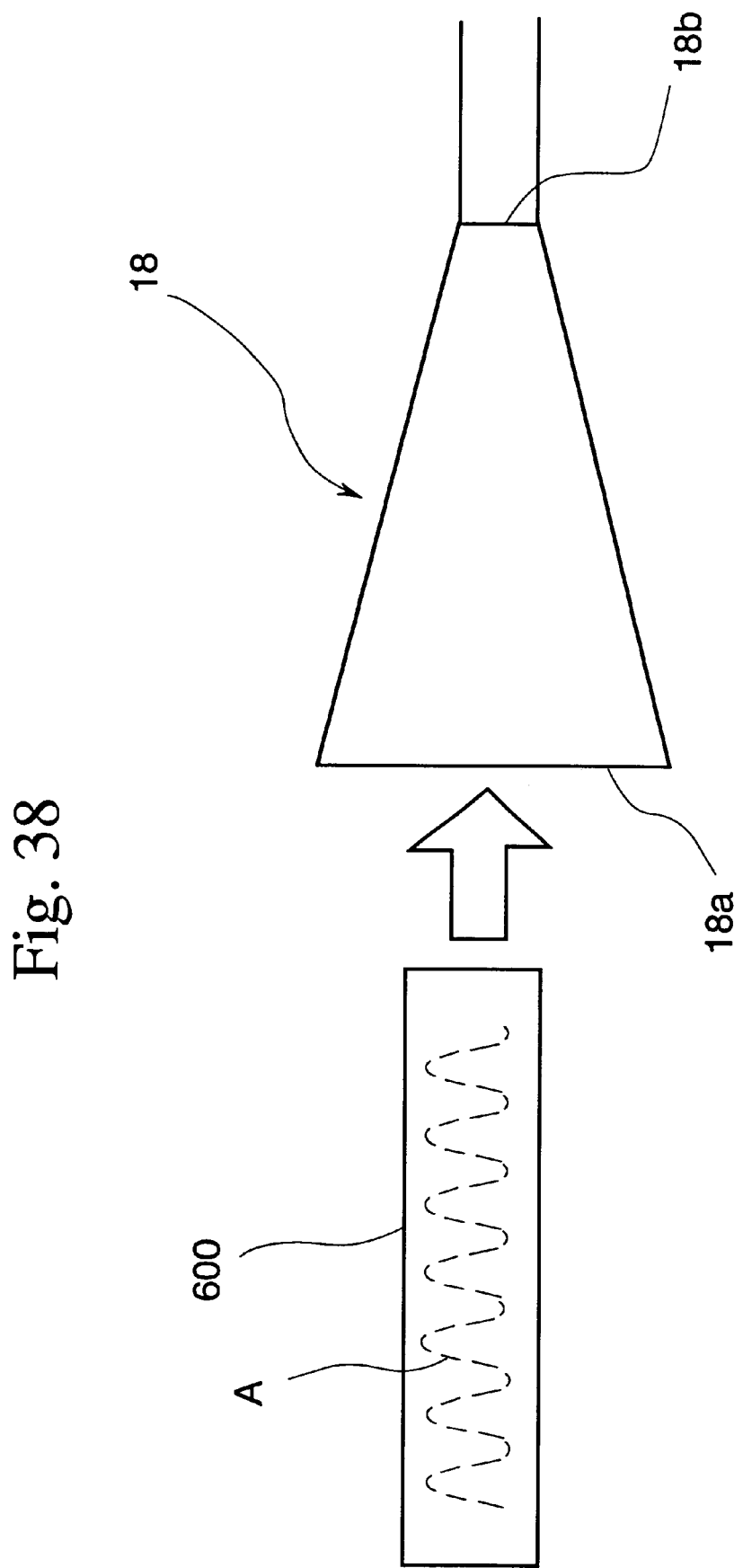
FIG. 38 shows a method of collapsing the artificial blood vessel in accordance with further different embodiment of the invention.
Figure 39:
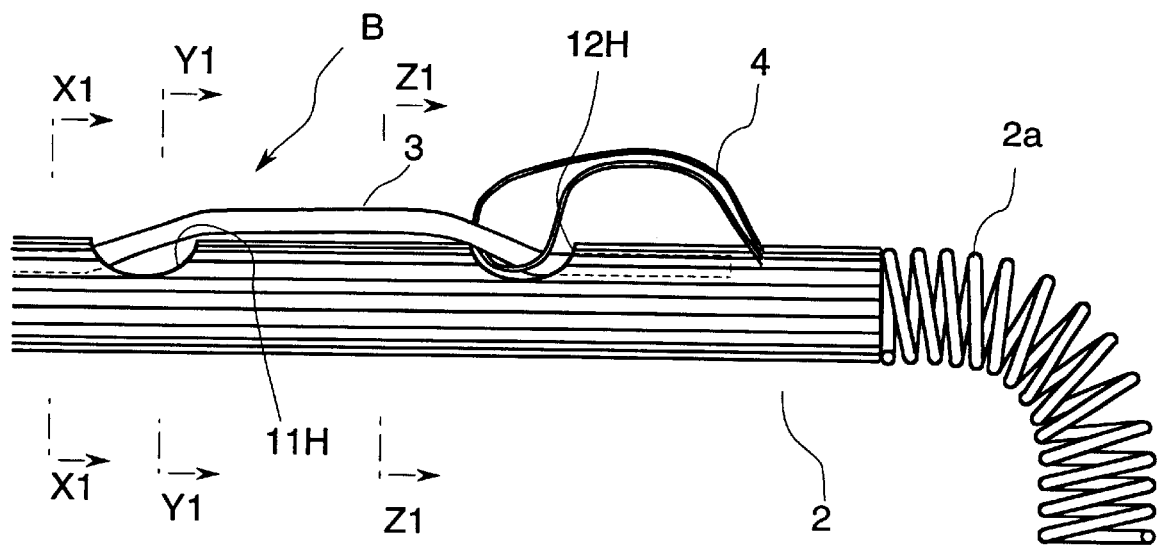
FIG. 39 is a view showing a modified form of a device for transporting the artificial blood vessel.
Figure 40:
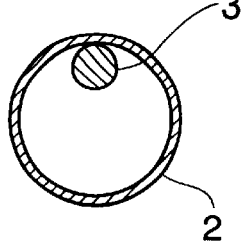
FIG. 40 is a cross-sectional view taken along the line X1—X1 of FIG. 39.
Figure 41:
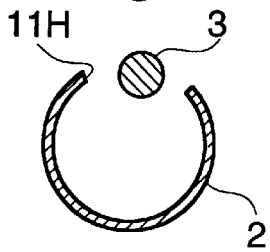
FIG. 41 is a cross-sectional view taken along the line Y1—Y1 of FIG. 39.
Figure 42:
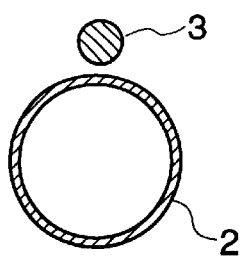
FIG. 42 is a cross-sectional view taken along the line Z1—Z1 of FIG. 39.
Figure 43:
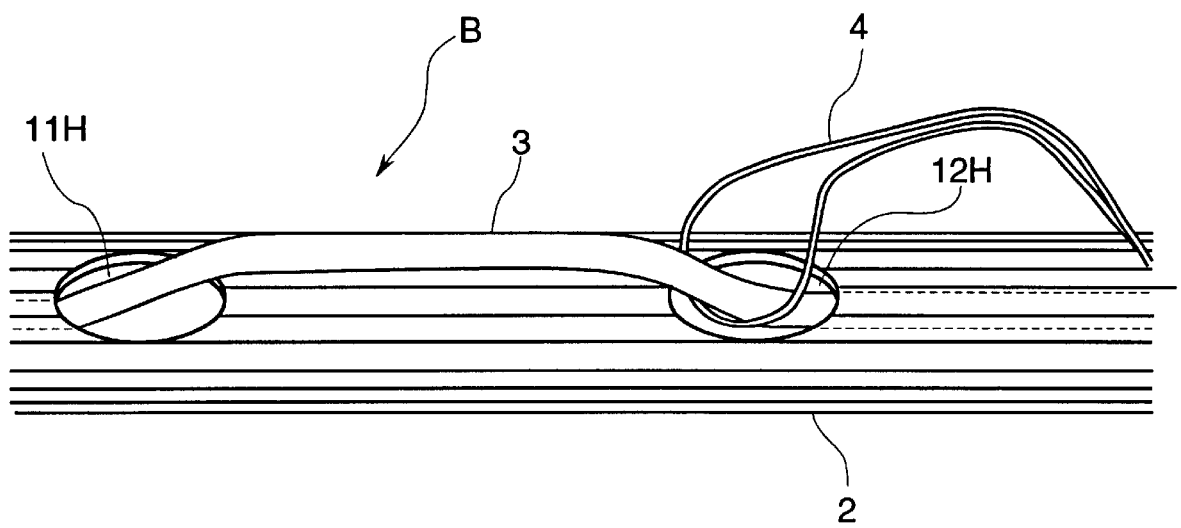
FIG. 43 is a view of the device for transporting the artificial blood vessel shown in FIG. 39 viewed from a different angle.

In order to collapse the artificial blood vessel A into a small size by inserting it into a funneled tube 18 from a large portion 18a toward a small portion 18b the artificial blood vessel A may be previously contained in a pipe member 600 having a diameter bigger than that of the small portion 18b of the funneled tube 18 and smaller than that of the large portion 18a of the funneled tube 18 as shown in FIG. 38. Just inserting the pipe member 600 into the funneled tube 18 so as to make abutting engagement with the inner surface of the funneled tube 18 and pulling out the artificial blood vessel A from the side of the front end wire ring enables the artificial blood vessel A to be collapsed into a smaller size so as to be inserted into the small portion 18b of the funneled tube 18 and a catheter.

Figure 44:
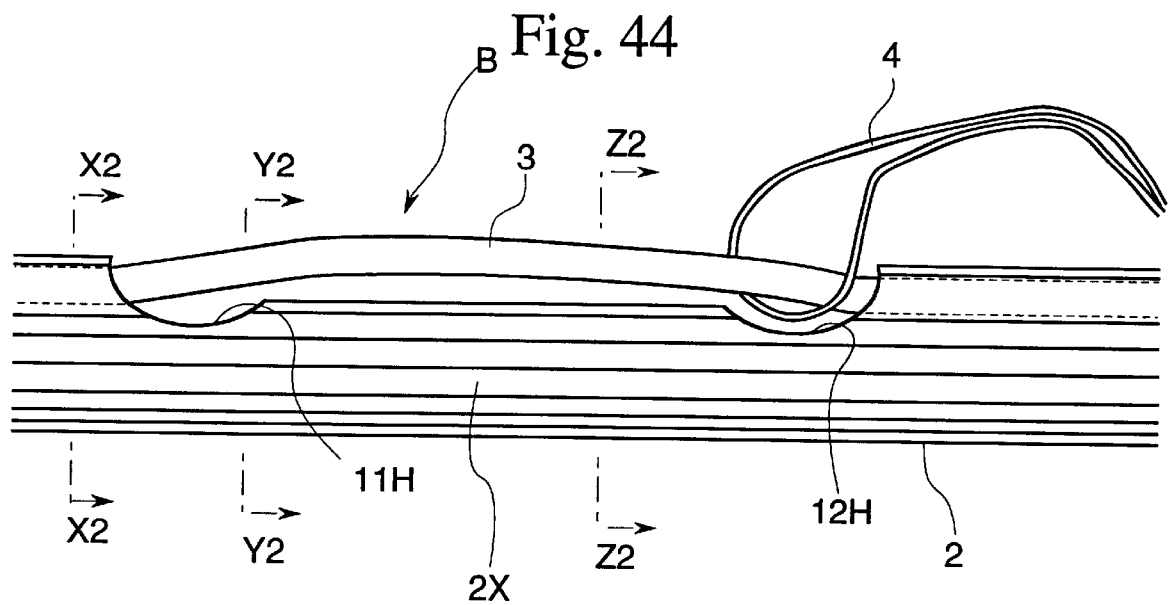
FIG. 44 is a view showing another modified form of the device for transporting an artificial blood vessel.
Figure 45:
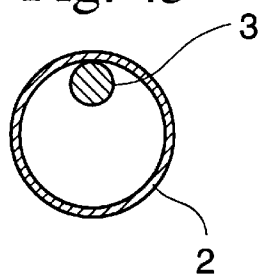
FIG. 45 is a cross-sectional view taken along the line X2—X2 of FIG. 44.
Figure 46:
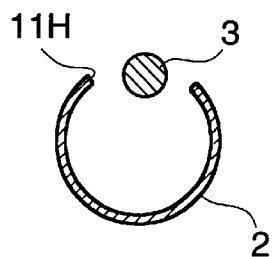
FIG. 46 is a cross-sectional view taken along the line Y2—Y2 of FIG. 44.
Figure 47:
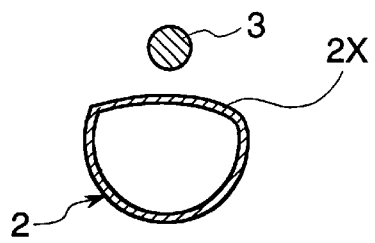
FIG. 47 is a cross-sectional view taken along the line Z2—Z2 of FIG. 44.
Figure 48:
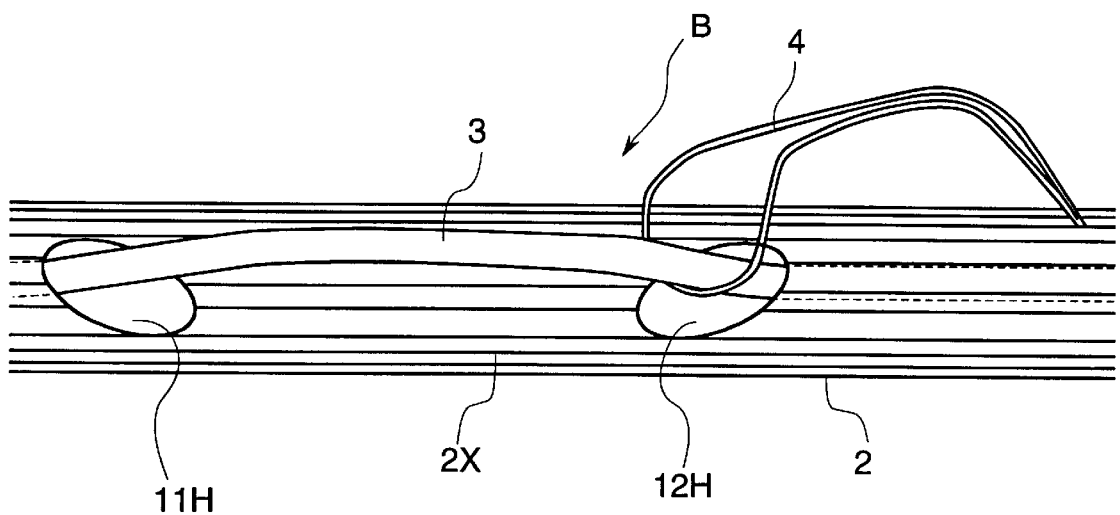
FIG. 48 is a view of the device for transporting the artificial blood vessel shown in FIG. 55 viewed from a different angle.
Figure 49:
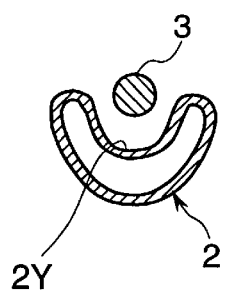
FIG. 49 is a cross-sectional view showing a modified form corresponding to FIG. 47.
Figure 50:
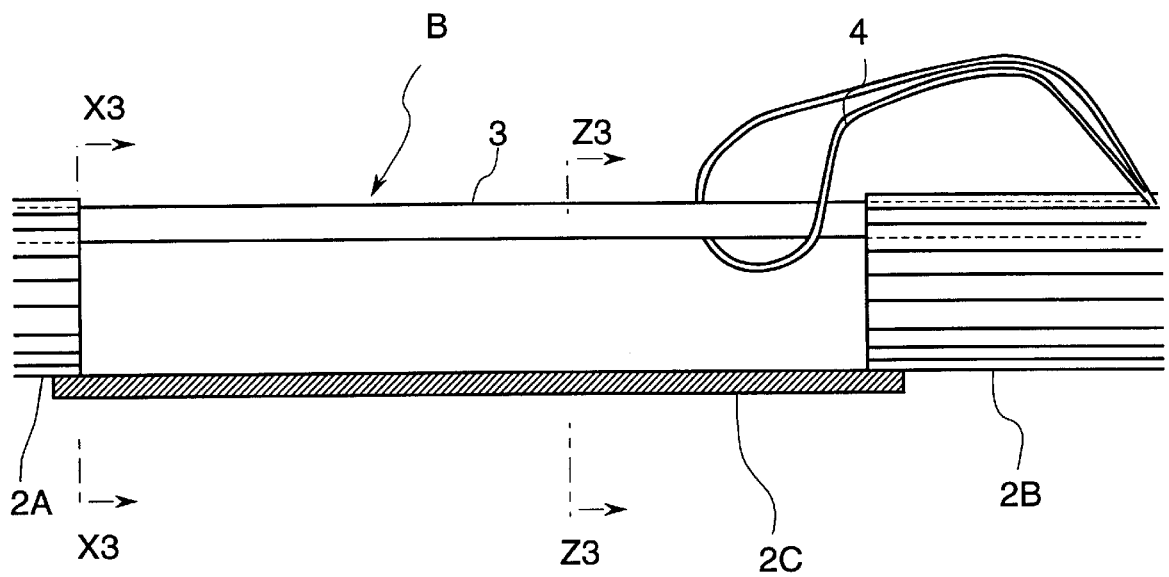
FIG. 50 is a view showing a further different modified form of the device for transporting the artificial blood vessel.
Figure 51:
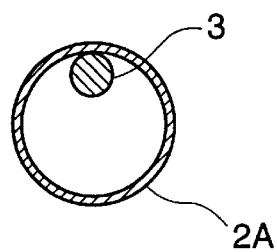
FIG. 51 is a cross-sectional view taken along the line X3—X3 of FIG. 50.
Figure 52:
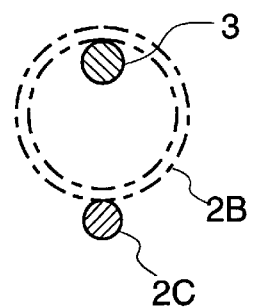
FIG. 52 is a cross-sectional view taken along the line Z3—Z3 of FIG. 50.
Figure 53:
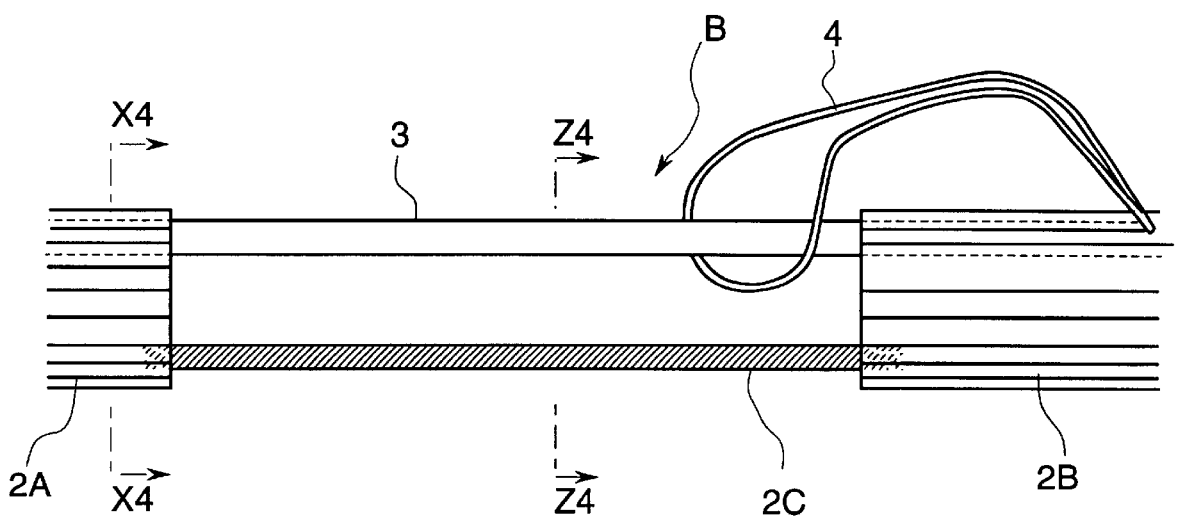
FIG. 53 is a view showing a further different modified form of the device for transporting the artificial blood vessel.
Figure 54:
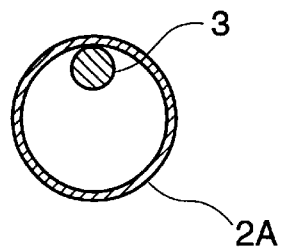
FIG. 54 is a cross-sectional view taken along the line Z4—Z4 of FIG. 53.
Figure 55:
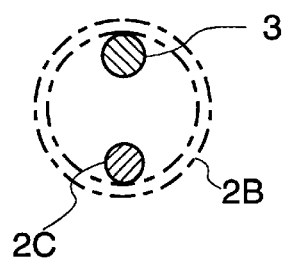
FIG. 55 is an end elevational view taken along the line Z3—Z3 of FIG. 53.

In each of above-described the embodiments, the device B for transporting the artificial blood vessel can be modified. The device B for transporting the artificial blood vessel comprises a flexible metallic tube 2 whose front end portion is connected to a helical spring 2a for guiding, a side window 1 formed adjacent the front end of the tube 2, a pair of strings 4 having both their ends fixed to the tube 2 adjacent the side window 1 and their middle portions formed into loops and a length of wire 3 slidably inserted into the tube 2. The side window formed in the tube 2, shown in FIGS. 39 through 43, comprises the first and the second opening holes 11H and 12H each spaced apart. The wire 3 pulled out of the tube 2 though the first opening hole 11H is hooked by the strings 4 and then introduced into the tube 2 through the second opening hole 12H. Thus arranged device B for transporting the artificial blood vessel does not require a big opening like the side window shown in FIG. 3. As a result of this, the tube 2 around the side window is thick enough to prevent bending, thereby effectively improving strength of the device B. In this case the cross section of the device B may have a flat portion 2X between the opening holes 11H and 12H as shown in FIGS. 44 though 48. With the device B having the flat portion 2X, the wire 3 pulled out of the first opening hole 11H can be inserted into the second opening hole 12H with the wire 3 remaining relatively straight. Then the wire 3 can effectively be prevented from bending and it also avoids a case that the wire 3 fails to be pulled out of the tube 2. FIG. 49 shows another cross section having a concaved portion 2Y. As a further different modified form shown in FIGS. 50 though 52, the tube 2 may comprise two tube elements 2A and 2B each spaced apart, and a connector 2C for connecting the outer circumferences of both tube elements 2A and 2B. No matter what arrangement the tube has, as far as the tube is strong enough as a whole, the device for transporting the artificial blood vessel can transport artificial blood vessels appropriately. The tube comprising two tube elements is especially effective for a tube having an extremely small diameter. If the tube of an extremely small diameter is provided with a side window, the window occupies most of the tube, which may weaken the strength of the tube. Consequently, the tube comprising two tube elements 2A and 2B can keep an appropriate strength as far as the material used for the connector 2C is strong enough. The connector 2C may connect the internal circumferences of two tube elements 2A and 2B as shown in FIGS. 53 through 55. The cross section of the connector 2C is not limited to a circle, but may be flat or flat having a partial ark. The two tube elements 2A and 2B may be connected by a plurality of the connector 2C, which are not shown in drawings.

Figure 56:
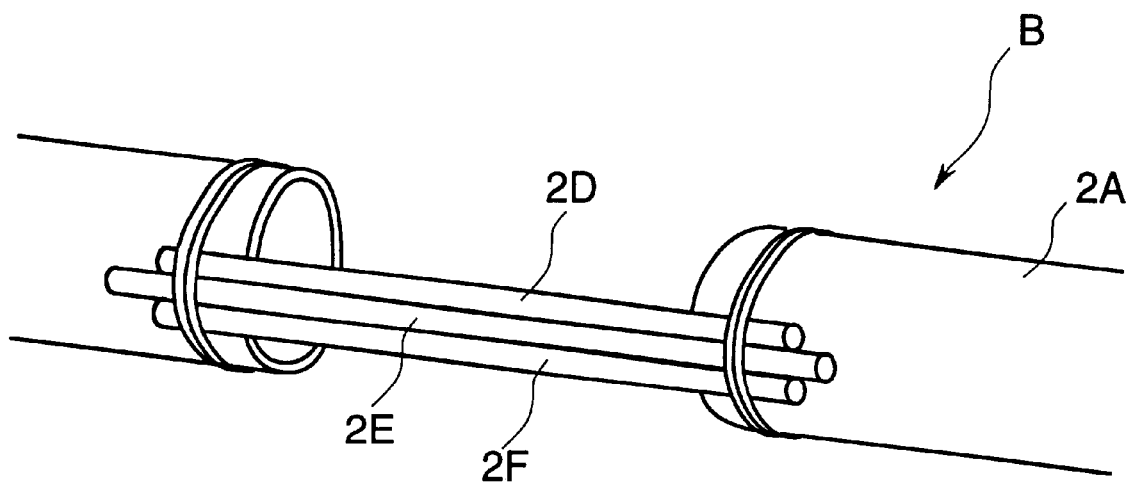
FIG. 56 is a view showing a further different modified form of the device for transporting the artificial blood vessel.
Figure 57:
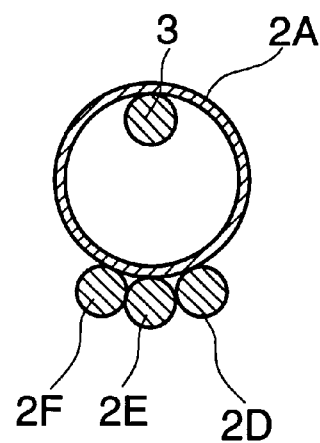
FIG. 57 is a cross-sectional view showing a modified form corresponding to FIG. 56.

In addition, as shown in FIGS. 56 and 57, the two tube elements 2A and 2B may be connected by three cylindrical connecting members 2D, 2E and 2F which constitute a tube connector, each of which is arranged along the outer circumference of the tube elements 2A, 2B and one connecting member 2E which locates the center is longer than the other connecting members 2D, 2F so as to project left and right. When the tube elements 2A, 2B are bent, an excessive force is not applied to a portion connecting the connecting members 2D, 2E, 2F and the tube elements 2A, 2B and an elastic force of the connecting members 2D, 2E, 2F will vary smoothly along the longitudinal direction around the connected portion, thereby to keep the tube elements 2A and 2B in a shape forming a natural curve.

Figure 58:
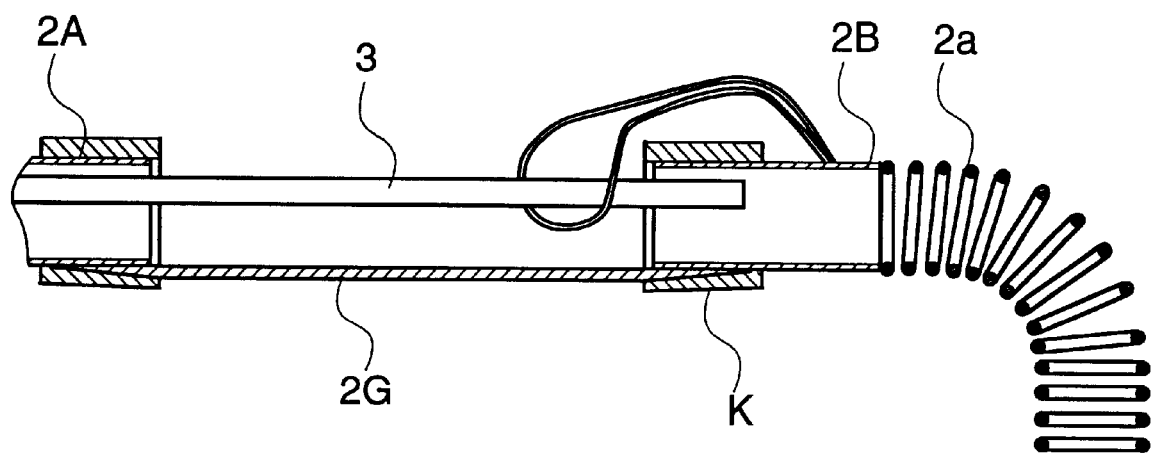
FIG. 58 is a cross-sectional view showing a further different modified form of the device for transporting the artificial blood vessel.

A cylindrical connecting member 2G which constitutes the tube connector may have, as shown in FIG. 58, both ends tapered to form a tapered portion in which a cross section thereof decreases gradually and outer circumference of the tapered portion and the tube elements 2A, 2B is covered by a cap K made of resin so as to connect the tube elements 2A and 2B. When the tube elements 2A, 2B are bent, a direction to which the cylindrical member 2G bends is not specified and a portion connecting the member 2G and the tube elements 2A, 2B can flexibly follow the movement of bending the tube element 2A, 2B, thereby to keep the tube elements 2A and 2B in a shape forming a natural curve without an excessive force applied to the connected portion.

Further, the device B for transporting the artificial blood vessel shown in FIGS. 39 through 58 may not have a string 4. In this case, the device B can pull the artificial blood vessel A effectively if the wire 3 is directly inserted into hooking means or a hole directly formed on the cover.

It is also effective if a part or whole of the catheter 8 is made of bellow, although not shown in figures.

A catheter 8 of a simple cylindrical shape is not only easy to break but also difficult to restore if once broken, which may lead to stricture in a body. While the catheter 8 made of bellow fits to a bent portion of the body easily with forming a natural curve, thereby to effectively avoid stricture in a body. Thus bellow-shaped catheter is suitable for transporting various kinds of appliances in addition to artificial blood vessels.

The device B for transporting the artificial blood vessel used in the above embodiments can be applied to transport various kinds of appliances in addition to artificial blood vessels so as to introduce them into a body.

POSSIBLE APPLICATIONS IN INDUSTRY

As mentioned above, the appliance to be implanted in accordance with the invention is valuable as an artificial blood vessel. It is possible to smoothly fold and restore the artificial blood vessel by the arrangement in which the front and rear end wire rings and at least the intermediate wire rings arranged adjacent to the front and rear end wire rings is connected with the cover so that the wire rings can make a back and forth movement relative to the cover within a certain range.

What is claimed is:

1. An appliance to be implanted comprising a front end wire ring, a rear end wire ring-arranged facing to the front end wire ring, a tubular cover which connects the front and rear end wire rings, and an intermediate wire ring arranged between the front and rear end wire rings, in which each of the wire rings is given flexibly foldable elasticity, and
   characterized by that the appliance to be implanted has an arrangement in which each of the front and rear end wire rings and at least the intermediate wire rings arranged adjacent to the front and rear end wire rings is connected with the cover through a film member so that each of the wire rings can make a back and forth movement relative to the cover within a certain range and that an annular gap formed between each of the wire rings and the cover is liquid-tightly sealed.

2. The appliance to be implanted, described in claim 1 and characterized by that said film member is bag-shaped in which whole of each wire rings is wrapped and that one end of said film member is attached to the cover almost to surround the outer circumference thereof so as to allow each of the wire rings to make a back and forth movement by making use of transformation of the film member.

3. The appliance to be implanted, described in claim 1 and characterized by that said film member is annular and each of the wire rings is attached along almost all of an outer circumferential end of the film member and an inner circumferential end of the film member is attached along almost all of the outer circumference of the cover so as to allow each of the wire rings to make a back and forth movement by making use of transformation of the film member.

4. The appliance to be implanted, described in claim 1 and characterized by that said film member has a long and narrow space therein along the direction of back and forth in which each of the wire rings is wrapped so as to allow each of the wire rings to make a back and forth movement inside the space relative to the cover.

5. The appliance to be implanted, described in claim 2 and characterized by that said film member has a wavy shape undulating along the direction of the circumference thereof and to a direction almost corresponding with a direction to which the wire rings are folded.

6. The appliance to be implanted, described in claim 1 and characterized by that said intermediate wire ring is wrapped in a mesh member, which is attached along almost all of an outer circumference of the cover.

7. The appliance to be implanted, described in claim 1, and characterized by that an expanding element is filled in a space between said film member and each of the wire rings.

8. The appliance to be implanted, described in claim 7 and characterized by that said expanding element is a fiber which surrounds an outer circumference of a wire which mainly constitutes said wire rings.

9. The appliance to be implanted, described in claim 7 and characterized by that said expanding element is a powder which is filled in a space between said film member and said wire rings.

10. The appliance to be implanted, described in claim 7, 8 or 9 and characterized by that said expanding element is super absorbing processed polymer which expands itself when absorbing liquid.

11. The appliance to be implanted, described in claim 1 and characterized by that an auxiliary wire ring is attached to the cover at a position almost corresponding to a position each of the wire ring is attached to the cover.

12. The appliance to be implanted, described in claim 11 and characterized by that the circumference of said auxiliary wire ring is divided into four or an even number over four, hooking means are formed for a front pull string to be passed through at every other dividing point, said auxiliary wire ring is folded into a wavy shape with the dividing points each of which is provided with a hooking means forming forwardly directed peaks and the other dividing points forming the bottoms of forwardly directed valleys, each of the other wire rings is folded into a wavy shape having the same phase as that of the auxiliary wire ring and the whole appliance to be implanted is inserted into a catheter.

13. The appliance to be implanted, described in claim 1 and characterized by that the circumference of the front end of said cover is divided into four or an even number over four and that hooking means are formed for a front pull string to be passed through at every other dividing point, said front end of the cover is folded into a wavy shape with the dividing points each of which is provided with a hooking means forming forwardly directed peaks and the other dividing points forming the bottoms of forwardly directed valleys, each of the front and rear end wire rings and the intermediate wire rings are folded into a wavy shape having the same phase as that of the front of the cover and the whole appliance to be implanted is inserted into a catheter.

14. The appliance to be implanted, described in claim 1 and characterized by that said appliance to be implanted is an artificial blood vessel.

15. The appliance to be implanted, described in claim 4 and characterized by that said film member has a wavy shape undulating along the direction of the circumference thereof and to a direction almost corresponding with a direction to which the wire rings are folded.

16. The appliance to be implanted, described in claim 2 and characterized by that an expanding element is filled in a space between said film member and each of the wire rings.

17. The appliance to be implanted, described in claim 3 and characterized by that an expanding element is filled in a space between said film member and each of the wire rings.

18. The appliance to be implanted, described in claim 4 and characterized by that an expanding element is filled in a space between said film member and each of the wire rings.

19. The appliance to be implanted, described in claim 5 and characterized by that an expanding element is filled in a space between said film member and each of the wire rings.

* * * * *

UNITED STATES PATENT AND TRADEMARK OFFICE
CERTIFICATE OF CORRECTION

PATENT NO. : 6,273,917 B1
DATED : August 14, 2001
INVENTOR(S) : Kanji Inoue

It is certified that error appears in the above-identified patent and that said Letters Patent is hereby corrected as shown below:

Column 19, claim 1,
Line 22, "ring-arranged" has been replaced with -- ring arranged --.

Signed and Sealed this

Ninth Day of April, 2002

Attest:

JAMES E. ROGAN
*Attesting Officer*   *Director of the United States Patent and Trademark Office*